(12) United States Patent
Misic et al.

(10) Patent No.: US 7,747,310 B2
(45) Date of Patent: Jun. 29, 2010

(54) SYSTEM AND METHOD OF OBTAINING IMAGES AND SPECTRA OF INTRACAVITY STRUCTURES USING 3.0 TESLA MAGNETIC RESONANCE SYSTEMS

(75) Inventors: George J. Misic, Allison Park, PA (US); Edward J. Rhinehart, Monroeville, PA (US)

(73) Assignee: Medrad, Inc., Indianola, PA (US)

( * ) Notice: Subject to any disclaimer, the term of this patent is extended or adjusted under 35 U.S.C. 154(b) by 1884 days.

(21) Appl. No.: 10/483,945

(22) PCT Filed: Mar. 13, 2003

(86) PCT No.: PCT/US03/07774

§ 371 (c)(1),
(2), (4) Date: Jan. 15, 2004

(87) PCT Pub. No.: WO03/098236

PCT Pub. Date: Nov. 27, 2003

(65) Prior Publication Data

US 2004/0236209 A1 Nov. 25, 2004

Related U.S. Application Data

(60) Provisional application No. 60/429,257, filed on Nov. 26, 2002, provisional application No. 60/381,727, filed on May 16, 2002.

(51) Int. Cl.
*A61B 5/055* (2006.01)

(52) U.S. Cl. ....................................... 600/423

(58) Field of Classification Search ................. 600/423, 600/410, 421, 433, 435, 424, 407; 324/300, 324/306, 307, 309, 314, 318, 320, 322
See application file for complete search history.

(56) References Cited

U.S. PATENT DOCUMENTS 2,085,644 A 6/1937 Fericot (Continued)

FOREIGN PATENT DOCUMENTS

DE 342 183 0 12/1985

(Continued)

OTHER PUBLICATIONS

International Search Report for Counterpart PCT Application PCT/US03/07774.

(Continued)

*Primary Examiner*—Eric F Winakur
*Assistant Examiner*—Vani Gupta
(74) *Attorney, Agent, or Firm*—James R. Stevenson

(57) ABSTRACT

An MR system features an intracavity probe and associated interface device. The probe includes a shaft, a balloon at one end thereof, and a coil loop within the balloon. The loop has two drive capacitors and a tuning capacitor, all of which in series. A junction node between the drive capacitors serves as a ground for electrically balancing the loop. Diametrically opposite the node, the tuning capacitor enables the loop to resonate at the operating frequency of the MR system. The interface allows the MR system to couple the loop to a port of the MR system during a receive cycle thereof and decouple it from the port during a transmit cycle thereof. With its balloon inserted and inflated within a cavity of a patient, the probe allows the MR system to generate images and/or spectra of the region of interest using the MR signals received by the loop.

21 Claims, 7 Drawing Sheets

U.S. PATENT DOCUMENTS

| | | | |
|---|---|---|---|
| 2,126,257 | A | 4/1938 | Hird |
| 3,800,802 | A | 4/1974 | Berry et al. |
| 4,338,942 | A | 7/1982 | Fogarty |
| 4,398,149 | A | 8/1983 | Zens |
| 4,545,390 | A | 10/1985 | Leary |
| 4,587,493 | A | 5/1986 | Sepponen |
| 4,617,936 | A | 10/1986 | Malko |
| 4,620,155 | A | 10/1986 | Edelstein |
| 4,633,181 | A | 12/1986 | Murphy-Boesch |
| 4,636,730 | A | 1/1987 | Bottomley |
| 4,646,024 | A | 2/1987 | Schenck et al. |
| 4,649,348 | A | 3/1987 | Flugan |
| 4,672,972 | A | 6/1987 | Berke |
| 4,680,549 | A | 7/1987 | Tanttu |
| 4,692,705 | A | 9/1987 | Hayes |
| 4,739,271 | A | 4/1988 | Haase |
| 4,764,726 | A | 8/1988 | Misic et al. |
| 4,775,371 | A | 10/1988 | Mueller, Jr. |
| 4,793,351 | A | 12/1988 | Landman et al. |
| 4,793,356 | A | 12/1988 | Misic et al. |
| 4,855,680 | A | 8/1989 | Arakawa et al. |
| 4,911,163 | A | 3/1990 | Fina |
| 4,920,318 | A | 4/1990 | Misic et al. |
| 4,928,064 | A | 5/1990 | Keren |
| 4,932,411 | A | 6/1990 | Fritschy et al. |
| 4,947,121 | A | 8/1990 | Hayes |
| 4,960,106 | A | 10/1990 | Kubokawa et al. |
| 4,989,608 | A | 2/1991 | Ratner |
| 5,035,231 | A | 7/1991 | Kubokawa et al. |
| 5,050,607 | A | 9/1991 | Bradley et al. |
| 5,071,406 | A | 12/1991 | Jang |
| 5,108,370 | A | 4/1992 | Walinsky |
| 5,170,789 | A | 12/1992 | Narayan et al. |
| 5,198,768 | A | 3/1993 | Keren |
| 5,271,400 | A | 12/1993 | Dumoulin et al. |
| 5,307,808 | A | 5/1994 | Dumoulin et al. |
| 5,307,814 | A | 5/1994 | Kressel et al. |
| 5,348,010 | A | 9/1994 | Schnall et al. |
| 5,355,087 | A | 10/1994 | Claiborne et al. |
| 5,365,928 | A | 11/1994 | Rhinehart et al. |
| 5,451,232 | A | 9/1995 | Rhinehart et al. |
| 5,476,095 | A | 12/1995 | Schnall et al. |
| 5,583,438 | A | 12/1996 | Eydelman et al. |
| 5,699,801 | A | 12/1997 | Atalar et al. |
| 5,928,145 | A | 7/1999 | Ocali et al. |
| 6,263,229 | B1 | 7/2001 | Atalar et al. |
| 6,408,202 | B1 | 6/2002 | Lima et al. |
| 6,501,980 | B1 | 12/2002 | Carlon et al. |
| 6,608,480 | B1 | 8/2003 | Weyers |
| 6,714,012 | B2 * | 3/2004 | Belt et al. .................. 324/318 |
| 6,766,185 | B2 * | 7/2004 | Scott .......................... 600/410 |
| 2002/0040185 | A1 | 4/2002 | Atalar et al. |

FOREIGN PATENT DOCUMENTS

| | | |
|---|---|---|
| EP | 0 214 721 | 3/1987 |
| EP | 0 249 338 | 12/1987 |
| JP | 61-90525 | 5/1986 |
| JP | 62-286451 | 12/1987 |
| JP | WO 88/00071 | 1/1988 |
| JP | 63-49150 | 3/1988 |
| JP | 63-270036 | 11/1988 |
| JP | 64-20832 | 1/1989 |
| WO | WO 84/01513 | 4/1984 |
| WO | WO 86/01093 | 2/1986 |
| WO | 8905115 | 6/1989 |
| WO | 03098236 | 11/2003 |

OTHER PUBLICATIONS

Press Release entitled, "Surgi-Vision Receives Fourth U. S. Patent Covering Its Intercept Internal Magnetic Resonance Imaging Coils," Surgi-Vision, Inc., Gaithersburg, MD (Aug. 8, 2001).

Product Brochure for The Leading Image, Torso Array for GE Signa 1.5T Phased Array Systems, Medrad, Inc., 87305-00-BA-16, Rev. B (no date).

John F. Schenck et al., "High Resolution Magnetic Resonance Imaging Using Surface Coils," Magnetic Resonance Annual 1986, Raven Press, New York (1986).

M. D. Schnall et al., "The Development of an Intracavity Inflatable Surface Coil for High Resolution Proton Imaging and Spectroscopy," Radiology, vol. 167, No. 1 (Apr. 1988).

Ronald J. Otto et al., "High Resolution MR Imaging of the Prostate," Society of Magnetic Resonance Imaging, UPN-47 (Feb. 1987).

Perinchery Narayan et al., "Transrectal Probe for 1H MRI and 31 P MR Spectroscopy of the Prostate Gland," Magnetic Resonance in Medicine, No. 2 (Aug. 11, 1989).

J. F. Martin et al., "Inflatable Surface Coil for MR Imaging of the Prostate," Radiology, vol. 167, No. 1 (Apr. 1988).

Supplemental European Search Report from counterpart application No. PCT/US05/041912, European application EP 05 856 978.1.

* cited by examiner

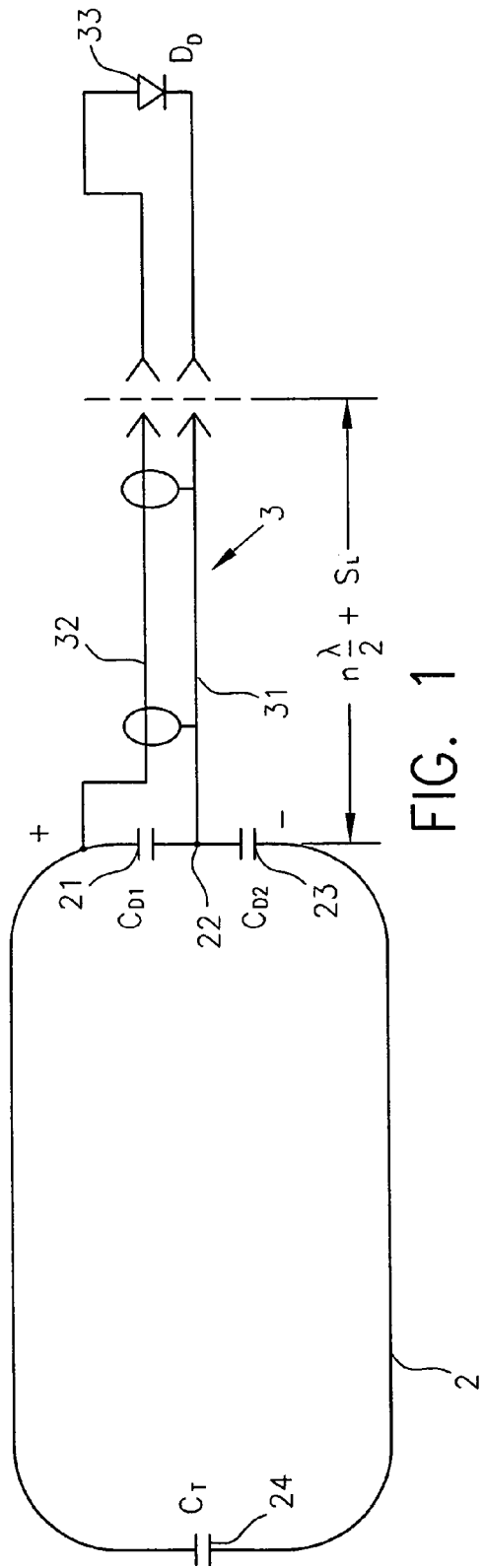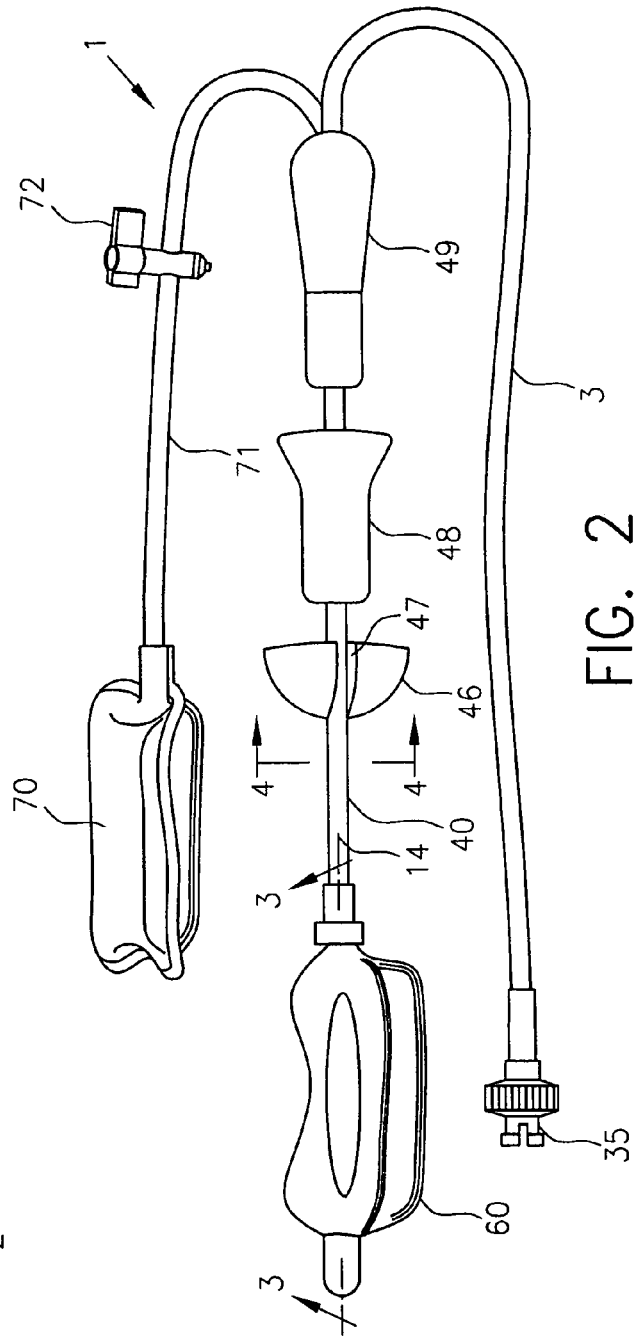

SYSTEM AND METHOD OF OBTAINING IMAGES AND SPECTRA OF INTRACAVITY STRUCTURES USING 3.0 TESLA MAGNETIC RESONANCE SYSTEMS

CROSS-REFERENCE TO RELATED APPLICATION(S)

This application claims the benefit of U.S. Provisional Applications 60/429,257 and 60/381,727, titled System And Method Of Obtaining Images And Spectra Of Intracavity Structures Using 3.0 Tesla Magnetic Resonance Systems and 3.0 Tesla Endorectal Coil And Interface For Single Receiver And Phased Array MR Scanning Of The Prostate And Other Pelvic Anatomy, respectively, filed on Nov. 26, 2002, and May 16, 2002, respectively. These provisional applications have been assigned to the assignee of the invention disclosed below, and their teachings are incorporated into this document by reference.

FIELD OF THE INVENTION

The present invention generally relates to systems and methods of obtaining images and spectra of intracavity structures using magnetic resonance (MR) systems. More particularly, the invention pertains to an intracavity probe capable of being inserted into various bodily openings, such as the rectum, vagina, mouth, etc., to obtain high resolution images of and spectroscopic results for regions of interest therein. Even more particularly, the invention relates to interface devices designed to interface such an intracavity probe with 2.0 Tesla to 5.0 Tesla MR systems to obtain such high resolution images and spectroscopic results for such regions of interest.

BRIEF DESCRIPTION OF RELATED ART

The following background information is provided to assist the reader to understand the invention disclosed below and the environment in which it will typically be used. The terms used herein are not intended to be limited to any particular narrow interpretation unless clearly stated otherwise, either expressly or impliedly, in this document.

Magnetic resonance imaging (MRI) is a noninvasive method of producing high quality images of the interior of the human body. It allows medical personnel to see inside the human body without surgery or the use of ionizing radiation such as X-rays. The images are of such high resolution that disease and other forms of pathology can often be visually distinguished from healthy human tissue. Magnetic resonance techniques and systems have also been developed for performing spectroscopic analyses by which the chemical content of tissue or other material can be ascertained.

MRI uses a powerful magnet, radio waves and computer technology to create detailed images of the soft tissues, muscles, nerves and bones in the human body. It does so by taking advantage of a basic property of the hydrogen atom, an atom that is found in abundance in all cells within the human body. In the absence of a magnetic field, the nuclei of hydrogen atoms spin like a top, or precess, randomly in every direction. When subject to a strong magnetic field, however, the spin-axes of the hydrogen nuclei align themselves in the direction of that field. This is because the nucleus of the hydrogen atom has what is referred to as a large magnetic moment, which is basically a strong inherent tendency to line up with the direction of the magnetic field. Collectively, the hydrogen nuclei of the area to be imaged create an average vector of magnetization that points parallel to the magnetic field.

A typical MRI system, or scanner, includes a main magnet, three gradient coils, a radio frequency (RF) antenna (often referred to as the whole body coil), and a computer station from which an operator can control the overall MRI system. The chief component of the MRI system, however, is the main magnet. It is typically superconducting in nature and cylindrical in shape. Within its cylindrical bore (into which patients are placed during an MRI procedure), the main magnet generates a strong magnetic field, often referred to as the $B_0$ field, which is both uniform and static (non-varying). This $B_0$ magnetic field is oriented along the longitudinal axis of the bore, referred to as the z direction, which compels the magnetization vectors of the hydrogen nuclei in the body to align themselves in that direction. In this alignment, the nuclei are prepared to receive RF energy of the appropriate frequency from the whole body coil. This frequency is known as the Larmor frequency and is governed by the equation $\omega = \gamma B_0$, where $\omega$ is the Larmor frequency (at which the hydrogen atoms precess), $\gamma$ is the gyromagnetic constant, and $B_0$ is the strength of the magnetic field.

The RF antenna, or whole body coil, is generally used both to transmit pulses of RF energy and to receive the resulting magnetic resonance (MR) signals induced thereby in the hydrogen nuclei. Specifically, during its transmit cycle, the body coil broadcasts RF energy into the cylindrical bore. This RF energy creates a radio frequency magnetic field, also known as the RF $B_1$ field, whose magnetic field lines are directed in a line perpendicular to the magnetization vector of the hydrogen nuclei. The RF pulse (or B1 field) causes the spin-axes of the hydrogen nuclei to tilt with respect to the main ($B_0$) magnetic field, thus causing the net magnetization vector to deviate from the z direction by a certain angle. The RF pulse, however, will affect only those hydrogen nuclei that are precessing about their axes at the frequency of the RF pulse. In other words, only the nuclei that "resonate" at that frequency will be affected, and such resonance is achieved in conjunction with the operation of the three gradient coils.

The gradient coils are electromagnetic coils. Each gradient coil is used to generate a linearly varying yet static magnetic field along one of the three spatial directions (x,y,z) within the cylindrical bore known as the gradient $B_1$ field. Positioned inside the main magnet, the gradient coils are able to alter the main magnetic field on a very local level when they are turned on and off very rapidly in a specific manner. Thus, in conjunction with the main magnet, the gradient coils can be operated according to various imaging techniques so that the hydrogen nuclei—at any given point or in any given strip, slice or unit of volume—will be able to achieve resonance when an RF pulse of the appropriate frequency is applied. In response to the RF pulse, the precessing hydrogen atoms in the selected region absorb the RF energy being transmitted from the body coil, thus forcing the magnetization vectors thereof to tilt away from the direction of the main ($B_0$) magnetic field. When the body coil is turned off, the hydrogen nuclei begin to release the RF energy in the form of the MR signal, as explained further below.

One well known technique that can be used to obtain images is referred to as the spin echo imaging technique. Operating according to this technique, the MRI system first activates one gradient coil to set up a magnetic field gradient along the z-axis. This is called the "slice select gradient," and it is set up when the RF pulse is applied and is shut off when the RF pulse is turned off. It allows resonance to occur only within those hydrogen nuclei located within a slice of the area being imaged. No resonance will occur in any tissue located on either side of the plane of interest. Immediately after the RF pulse ceases, all of the nuclei in the activated slice are "in phase," i.e., their magnetization vectors all point in the same direction. Left to their own devices, the net magnetization vectors of all the hydrogen nuclei in the slice would relax, thus realigning with the z direction. Instead, however, the second gradient coil is briefly activated to create a magnetic field gradient along the y-axis. This is called the "phase encoding gradient." It causes the magnetization vectors of the nuclei within the slice to point, as one moves between the weakest and strongest ends of the gradient, in increasingly different directions. Next, after the RF pulse, slice select gradient and phase encoding gradient have been turned off, the third gradient coil is briefly activated to create a gradient along the x-axis. This is called the "frequency encoding gradient" or "read out gradient," as it is only applied when the MR signal is ultimately measured. It causes the relaxing magnetization vectors to be differentially re-excited, so that the nuclei near the low end of the gradient begin to precess at a faster rate, and those at the high end pick up even more speed. When these nuclei relax again, the fastest ones (those which were at the high end of the gradient) will emit the highest frequency of radio waves.

Collectively, the gradient coils allow the MR signal to be spatially encoded, so that each portion of the area being imaged is uniquely defined by the frequency and phase of its resonance signal. In particular, as the hydrogen nuclei relax, each becomes a miniature radio transmitter, giving out a characteristic pulse that changes over time, depending on the local microenvironment in which it resides. For example, hydrogen nuclei in fats have a different microenvironment than do those in water, and thus transmit different pulses. Due to these differences, in conjunction with the different water-to-fat ratios of different tissues, different tissues transmit radio signals of different frequencies. During its receive cycle, the body coil detects these miniature radio transmissions, which are often collectively referred to as the MR signal. From the body coil, these unique resonance signals are conveyed to the receivers of the MR system where they are converted into mathematical data corresponding thereto. The entire procedure must be repeated multiple times to form an image with a good signal-to-noise ratio (SNR). Using multi-dimensional Fourier transformations, an MR system can convert the mathematical data into a two- or even a three-dimensional image.

When more detailed images of a specific part of the body are needed, a local coil is often used in addition to, or instead of, the whole body coil. A local coil can take the form of a volume coil or a surface coil. A volume coil is used to surround or enclose the volume to be imaged (e.g., a head, an arm, a wrist, a leg, a knee or other region of interest). A surface coil, however, is merely fitted or otherwise placed against a particular surface of the patient so that the underlying region of interest can be imaged (e.g., the abdominal, thoracic and/or pelvic regions). In addition, a local coil can be designed to operate either as a receive-only coil or a transmit/receive (T/R) coil. A receive-only coil is only capable of detecting the MR signals produced by the human body (in response to the $B_1$ magnetic field generated by the MR system during a scanning procedure). A T/R coil, however, is capable of both receiving the MR signals as well as transmitting the RF pulses that produce the RF $B_1$ magnetic field, which is the prerequisite for inducing resonance in the tissues of the region of interest.

It is well known in the field of MRI to use a single local coil, whether surface or volume, to detect the MR signals. According to the single coil approach, a relatively large local coil is used to cover or enclose the entire region of interest. Early receiving coils were just linear coils, meaning that they could detect only one of the two (i.e., vertical $M_{x'}$ and horizontal $M_{y'}$) quadrature components of the MR signals produced by the region of interest. Subsequent receiving coils, however, employed quadrature mode detection, meaning that they could intercept both the vertical and horizontal components. Compared to linear receiving coils, quadrature receiving coils enabled MRI systems to provide images for which the SNR was much improved, typically by as much as 41%. Even with the improvement brought with quadrature mode detection, the single coil approach still provided images whose quality invited improvement. The disadvantage inherent to the single coil approach is attributable to just one coil structure being used to acquire the MR signals over the entire region of interest.

Phased array coils were developed to overcome the shortcomings with the single coil approach. Instead of one large local coil, the phased array approach uses a plurality of smaller local coils, with each such coil covering or enclosing only a portion of the region of interest. In a system having two such coils, for example, each of the coils would cover or enclose approximately half of the region of interest, with the two coils typically being partially overlapped for purposes of magnetic isolation. The two coils would acquire the MR signals from their respective portions simultaneously, and they would not interact adversely due to the overlap. Because each coil covers only half of the region of interest, each such coil is able to receive the MR signals at a higher SNR ratio for that portion of the region of the interest within its coverage area. The smaller local coils of the phased array thus collectively provide the MRI system with the signal data necessary to generate an image of the entire region of interest that is higher in resolution than what can be obtained from a single large local coil.

One example of a phased array coil is the Gore® torso array produced by W.L. Gore and Associates, Inc. The torso array contains four surface coils, two of which disposed in an anterior paddle and the other two disposed in a posterior paddle. The two paddles are designed to be placed against the anterior and posterior surfaces, respectively, of the patient about the abdominal, thoracic and pelvic regions. The torso array is designed for use with an MR system whose data acquisition system has multiple receivers. The four leads of the torso array, one each from the two anterior surface coils and the two posterior surface coils, can be connected to separate receivers, with each receiver amplifying and digitizing the signal it receives. The MR system then combines the digitized data from the separate receivers to form an image whose overall SNR is better than what could be obtained from a single local coil, or even two larger anterior and posterior local coils, covering the entire region of interest alone.

It is also well known to obtain images of internal bodily structures through the use of intracavity probes. An example of a prior art intracavity probe can be found in U.S. Pat. Nos. 5,476,095 and 5,355,087. both of which are assigned to the assignee of the present invention and incorporated herein by reference. The prior art probe disclosed in those patents is designed to be inserted into bodily openings such as the rectum, vagina, and mouth. Those patents also disclose interface devices that are designed to interface the prior art intracavity probe with MR imaging and spectroscopy systems. A method of using the intracavity probe is disclosed in U.S. Pat. No. 5,348,010. which is also assigned to the assignee of the present invention and incorporated herein by reference.

The prior art probe, operated in conjunction with its associated interface unit, allows an MR system to generate images of, and spectroscopic results for, various internal bodily structures such as the prostate gland, colon or cervix. Examples of such prior art probes include the BPX-15 prostate/endorectal coil (E-coil), the PCC-15 colorectal coil, and the BCR-15 cervix coil, all of which are part of the MRInnervu® line of disposable coils produced by Medrad, Inc. of Indianola, Pa. Examples of such interface units include the ATD-II and the ATD-Torso units, also produced by Medrad, Inc.

The ATD-II unit is used to interface the prior art probe with one receiver of an MR system to provide images or spectra of the region of interest, namely, the prostate gland, colon or cervix. The ATD-Torso unit is used to interface not only the prior art probe but also the Gore® torso array with multiple receivers of the MR system. When connected to such a probe and the torso array, the ATD-Torso unit allows the MR system to provide images or spectra not only of the prostate gland, colon or cervix but also of the surrounding anatomy, i.e., the abdominal, thoracic and pelvic regions.

Despite their widespread acceptance and good reputation in the marketplace, these prior art intracavity probes and interfaces units nevertheless have a few shortcomings. First, the prior art probe and its associated interface units (i.e., ATD-II and ATD Torso units) are designed to operate only with 1.0 or 1.5 Tesla MR systems. Consequently, they are not suitable for use with MR systems designed to operate at higher field strengths, such as the 2.0 to 5.0 Tesla and particularly 3.0 Tesla MR systems that are capable of producing even higher quality images and spectrographic results. Second, as a result of that design constraint, the prior art intracavity probe was designed with a coil loop that exhibits a 750 to 1000 ohm output impedance. Consequently, the interface units for the prior art probe had to include a $\pi$ network or similar circuitry to match the high output impedance of the coil loop to the low input impedance (e.g., 50 ohms) required by various MR systems. Third, the design of the prior art probe allowed the tuning of its coil loop to deviate from the operating frequency of the MR system, the extent to which depending on the particular conditions (e.g., patients) in which the probe was used. Therefore, the prior art interface units for the prior art probe typically had to include tuning circuitry so as to assure that the intracavity probe could be tuned to the operating frequency of the MR system under all operating conditions.

OBJECTIVES OF THE INVENTION

It is, therefore, an objective of the invention to provide an intracavity probe, capable of being used with magnetic resonance (MR) systems designed to operate at 2.0 to 5.0 Tesla field strengths at least and particularly at 3.0 Tesla field strengths.

Another objective of the invention is to provide an intracavity probe having a coil loop with a broader frequency response than prior art intracavity probes, with little or even no sacrifice of signal-to-noise ratio, thereby obviating the need to tune the coil loop on a per patient or per coil basis as is required of such prior art probes.

Yet another objective is to provide an interface device that interfaces such an intracavity probe with such an MR system to obtain high resolution images of and spectroscopic results for the region of interest, without the need to tune the probe.

Still another objective is to provide an interface device that is designed to interface not only such an intracavity probe but also a phased array coil system, such as the Gore® torso array, with such an MR system.

A further objective of the invention is to provide a method of obtaining images and/or spectra of a region of interest within a cavity of a patient using such an intracavity probe, an interface device and an MR system.

One other objective of the invention is to provide a method of making such an intracavity probe for use with such an MR system with which to obtain images and/or spectra of a region of interest within a cavity of a patient.

Yet another objective is to provide an intracavity probe that is disposable in that it does not contain the relatively expensive decoupling components, which are instead incorporated into a reusable interface device with which the probe shall interface.

Still another objective is to provide an intracavity probe as an endorectal probe designed to be inserted into the rectum to obtain images and/or spectra of the male prostate gland.

A further objective is to provide an intracavity probe capable of being inserted into any one or more of various bodily openings, such as the rectum, vagina, mouth, etc., to obtain high resolution images of and spectroscopic results for the region of interest.

In addition to the objectives and advantages listed above, various other objectives and advantages of the invention will become more readily apparent to persons skilled in the relevant art from a reading of the detailed description section of this document. The other objectives and advantages will become particularly apparent when the detailed description is considered along with the drawings and claims presented below.

SUMMARY OF THE INVENTION

The foregoing objectives and advantages are attained by the various embodiments and related aspects of the invention summarized below.

In one aspect of a presently preferred embodiment, the invention provides an intracavity probe for use with a magnetic resonance (MR) system for obtaining images or spectra of a region of interest within a cavity of a patient. The probe includes a coil loop and an output cable. Designed to receive MR signals from the region of interest, the coil loop has a plurality of capacitors including first and second drive capacitors and a tuning capacitor. The first and second drive capacitors are serially connected within the coil loop and at a junction node thereof form a virtual ground for electrically balancing and impedance matching the coil loop. The two drive capacitors are of approximately equal value. The tuning capacitor is serially connected within the coil loop diametrically opposite the junction node of the drive capacitors. The tuning capacitor has a value selected to resonate the coil loop at an operating frequency of the MR system. The output cable connects the coil loop to an interface device for the intracavity probe. The output cable at one end connects across one of the drive capacitors and at its other end has a plug for connection to the interface device. The output cable has an electrical length of $n(\lambda/2)+S_L$ wherein n is an integer, $\lambda$ is a wavelength of the operating frequency of the MR system, and $S_L$ is a supplemental length whose reactance is equal in magnitude to that of one of the drive capacitors.

In a broader application, the invention provides a magnetic resonance (MR) system comprising an MR scanner, an intracavity probe and an interface device. Designed to be inserted within a cavity of a patient, the intracavity probe includes a shaft, an inflatable balloon and a coil loop. The balloon is connected to a distal end of the shaft, and the coil loop secured within the balloon approximate an underside of its anterior surface. The anterior surface of the balloon is conformable to an interior contour of the cavity, and a posterior surface of the balloon is used for positioning the balloon within the cavity. When the balloon is inflated, the posterior surface presses against a wall of the cavity that is generally opposite a region of interest within the cavity. This forces the anterior surface of the balloon against the interior contour of the cavity thereby bringing the coil loop approximate the region of interest for optimal reception of MR signals therefrom. The coil loop has a plurality of capacitors including first and second drive capacitors and a tuning capacitor. The first and second drive capacitors are serially connected within the coil loop and at a junction node thereof form a virtual ground for electrically balancing and impedance matching the coil loop. The two drive capacitors are of approximately equal value. The tuning capacitor is serially connected within the coil loop diametrically opposite the junction node of the drive capacitors. The tuning capacitor has a value selected to resonate the coil loop at an operating frequency of the MR system. The MR scanner is used to generate image(s) or spectra of the region of interest using the MR signals received by the coil loop from the region of interest. The interface device has a probe interface circuit for electrically interconnecting the intracavity probe and the MR system. The probe interface circuit features a PIN diode capable of being biased by the MR system by which the coil loop can be (i) coupled to a probe input port of the MR system during a receive cycle thereof and (ii) decoupled from the probe input port during a transmit cycle thereof.

In another aspect of the presently preferred embodiment, the invention provides an interface device for interfacing an intracavity probe with a (probe) input port of a magnetic resonance (MR) system which is not equipped with its own preamplifier. The probe has a output cable for connecting its coil loop to the interface device. The interface device includes a PIN diode and a preamplifier. The MR system can bias the PIN diode so that the coil loop is (i) coupled to the probe input port during a receive cycle of the MR system and (ii) decoupled from the probe input port during a transmit cycle of the MR system. The preamplifier provides gain and impedance matching between an anode of the PIN diode and the probe input port of the MR system so that with enhancement of signal-to-noise ratio the MR signals received by the coil loop are passed to the probe input port of the MR system.

In yet another aspect of the presently preferred embodiment, the invention provides an interface device for interfacing both an intracavity probe and a coil system with a magnetic resonance (MR) system. The intracavity probe features an output cable for connecting a coil loop of the probe to the interface device. The interface device allows the probe via its output cable to be interfaced with a (probe) input port of the MR system which is equipped with its own preamplifier. The interface device includes a PIN diode and an array interface circuit. The MR system can bias the PIN diode so that the coil loop is (i) coupled to the probe input port during a receive cycle of the MR system and (ii) decoupled from the probe input port during a transmit cycle of the MR system. The array interface circuit is used to electrically interconnect the coil system and the MR system. The array interface circuit includes first and second series resonant networks, a pair of ¼ wavelength networks and a ¼ wavelength combiner. The first series resonant network is for conveying MR signals from a first coil of the coil system to the first coil input port of the MR system. The second series resonant network is for conveying MR signals from a second coil of the coil system to the second coil input port of the MR system. One of the ¼ wavelength networks is for receiving MR signals from a third coil of the coil system, and the other ¼ wavelength network is for receiving MR signals from a fourth coil of the coil system. The ¼ wavelength combiner is used to combine the MR signals received from the pair of ¼ wavelength networks and convey the combined MR signals to the third coil input port.

The invention also provides a preferred method of obtaining images or spectra of a region of interest within a cavity of a patient using a magnetic resonance (MR) system. The method includes the steps of providing an intracavity probe and providing an output cable. The intracavity probe shall have (i) a flexible shaft, (ii) an inflatable balloon that connects to an end of the flexible shaft, and (iii) a coil loop secured within the balloon approximate an underside of an anterior surface thereof and capable of receiving MR signals from the region of interest. The anterior surface of the balloon is conformable to a contour of the cavity, and a posterior surface of the balloon features at least a pair of undulating folds. The coil loop has a plurality of capacitors including first and second drive capacitors and a tuning capacitor. The first and second drive capacitors are serially connected within the coil loop and at a junction node thereof form a virtual ground for electrically balancing and impedance matching the coil loop. The two drive capacitors are of approximately equal value. The tuning capacitor is serially connected within the coil loop diametrically opposite the junction node of the drive capacitors. The tuning capacitor has a value selected to resonate the coil loop at an operating frequency of the MR system. The method also includes the step of providing an output cable for connecting the coil loop to an external circuit with which said intracavity probe is connected to the MR system. Another step involves inserting the intracavity probe into a position within the cavity of the patient so that the anterior surface of the balloon is in proximity to the region of interest. The next step involves inflating the balloon and thereby force the undulating folds to unfold against a wall of the cavity generally opposite the region of interest. This forces the anterior surface of the balloon against the contour of the cavity and securely positions the coil loop approximate the region of interest for optimal reception of the MR signals therefrom. Subsequent steps involve inducing the region of interest to emit the MR signals, and using the coil loop to sense the MR signals induced within the region of interest. The method also includes the step of generating image(s) and spectra of the region of interest using the MR signals received therefrom.

The invention further provides a preferred method of making an intracavity probe for use with a magnetic resonance (MR) system with which to obtain images or spectra of a region of interest from within a cavity of a patient. The method includes the steps of choosing a size of a coil loop of the probe to permit the probe to be suitable for insertion into the cavity, and temporarily inserting a variable capacitor in serial connection within the coil loop. The method also involves the steps of subjecting the coil loop to an operating frequency of the MR system, and then adjusting the variable capacitor to a resonance value at which the coil loop resonates. At this operating frequency, the capacitive reactance of the coil loop will equal in magnitude the inductive reactance of the coil loop. Related steps involve measuring a quality factor of the coil loop when the coil loop is loaded, and then determining a series resistance of the coil loop using the quality factor so measured and an inductive reactance of the coil loop when loaded. The matching value for a matching capacitor is then calculated, so as to match an output impedance of the probe with an impedance required by an external circuit with which the intracavity probe shall interface. The method also includes the step of inserting two drive capacitors of the matching value into the coil loop in series with each other to form a junction node whereat the drive capacitors connect. The junction node is connectable to a shield conductor of an output cable, and an opposite node of one of the drive capacitors is connectable to a center conductor of the output cable. A tuning capacitor is then selected so that a total capacitance of the coil loop is equal to the resonance value. The variable capacitor is then replaced with the tuning capacitor. The tuning capacitor is serially connected within the coil loop diametrically opposite the junction node of two drive capacitors. The junction node thus forms a virtual ground for electrically balancing the coil loop.

It should be understood that the present invention is not limited to the presently preferred embodiment(s) and related aspects discussed above.

BRIEF DESCRIPTION OF THE DRAWINGS

The invention and its presently preferred and alternative embodiments will be better understood by reference to the detailed disclosure below and to the accompanying drawings, wherein:

FIG. 1 is a schematic diagram of a coil loop and an output cable of an intracavity probe according to one aspect of the presently preferred embodiment of the invention;

FIG. 2 is a perspective view showing the intracavity probe of FIG. 1 in its fully assembled and fully equipped state;

DETAILED DESCRIPTION OF THE INVENTION

Figure 3:
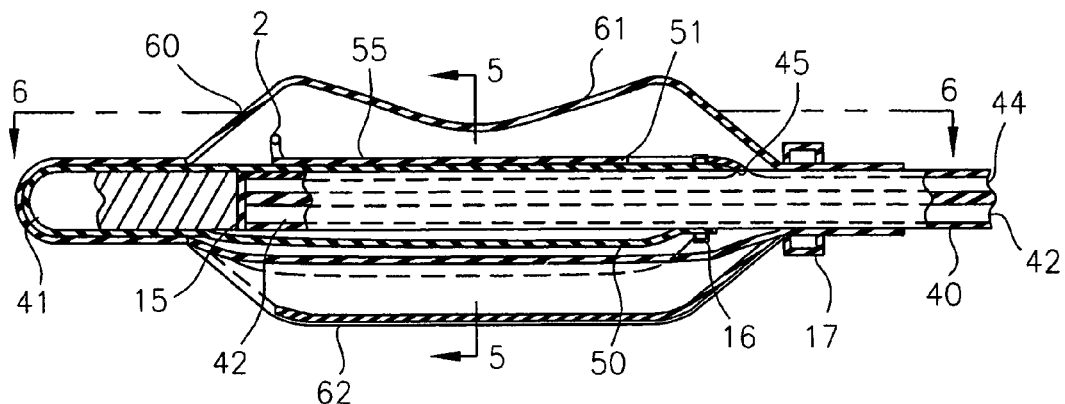
FIG. 3 is a cross-sectional view of the intracavity probe taken through line 3-3 of FIG. 2 showing a distal end of the probe and inflatable balloon(s) attached thereto.

In all of its embodiments and related aspects, the present invention disclosed below is ideally used with magnetic resonance (MR) systems designed to operate at 3.0 Tesla field strengths, though it is also applicable to those operable from approximately 2.0 to 5.0 T. For purposes of illustration below, the invention will be described in the context of the 3.0T systems produced by General Electric Medical Systems (GEMS).

FIGS. 1-7 illustrate one aspect of a presently preferred embodiment of the invention, namely, an intracavity probe, generally designated 1. The probe is intended for use with an MR system to obtain images or spectra of a region of interest within a cavity of a patient. It is described herein in a specific implementation, i.e., as an endorectal probe designed to be inserted into the rectum to obtain images and/or spectra of the male prostate gland. Although presented herein as an endorectal probe, it should be understood that the invention is equally capable of being adapted to obtain images of and/or spectra from other regions of interest such as those accessible through the mouth, the vagina or other orifices penetrable by an intracavity probe. The principles presented herein may also be applied to MR imaging or spectroscopic techniques appropriate for the arteries, veins, and other structures of the body. Whatever the application, the receiving coil within intracavity probe will need to be housed in, or otherwise incorporated into, a package appropriately designed to conform to the target anatomy.

In its most novel aspects as best shown in FIG. 1, intracavity probe 1 includes a coil loop 2 and an output cable 3. Ideally made of a conductive material that is flexible, coil loop 2 is preferably a single turn coil capable of picking up radio frequency (RF) signals. Designed to receive magnetic resonance RF signals from the region of interest, coil loop 2 has a plurality of capacitors including first drive capacitor 21, second drive capacitor 23, and tuning capacitor 24. The first and second drive capacitors are serially connected within coil loop 2. As is explained below, the junction node 22 at which drive capacitors 21 and 23 connect forms a virtual ground for electrically balancing and impedance matching the coil loop 2. Tuning capacitor 24 is also serially connected within coil loop 2 but diametrically opposite the junction node 22 of capacitors 21 and 23. Tuning capacitor 24 is selected to resonate coil loop 2 at an operating frequency of the MR system, which for a 3.0 Telsa scanner would be approximately 128 MHz.

Figure 8:
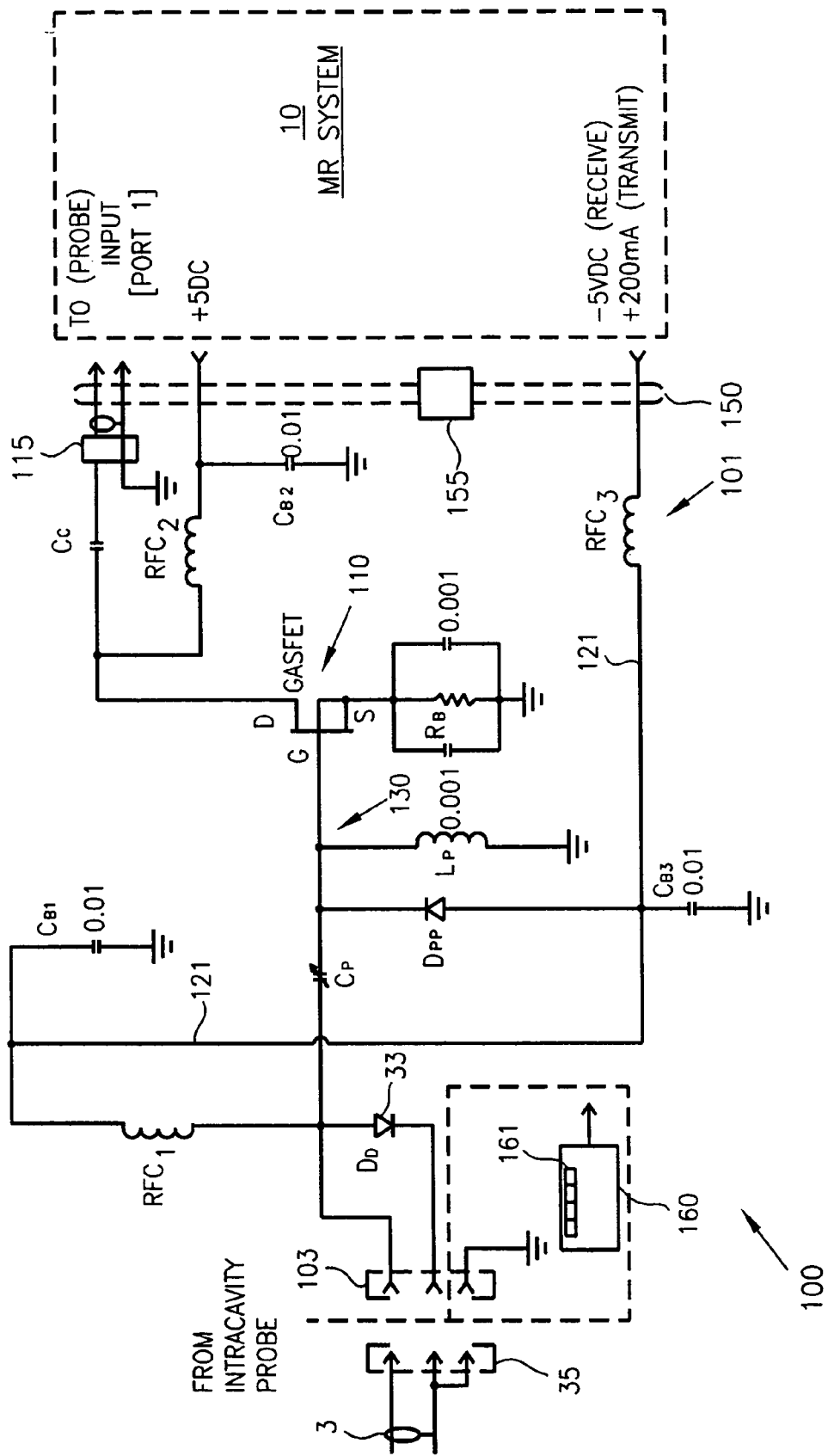
FIG. 8 is a schematic diagram of an interface device according to another aspect of the presently preferred embodiment of the invention wherein, in its single-receiver version, the interface device has a probe interface circuit for interfacing the intracavity probe of FIGS. 1-7 with a (probe) input port of a magnetic resonance (MR) system which is not equipped with its own preamplifier.
Figure 9:
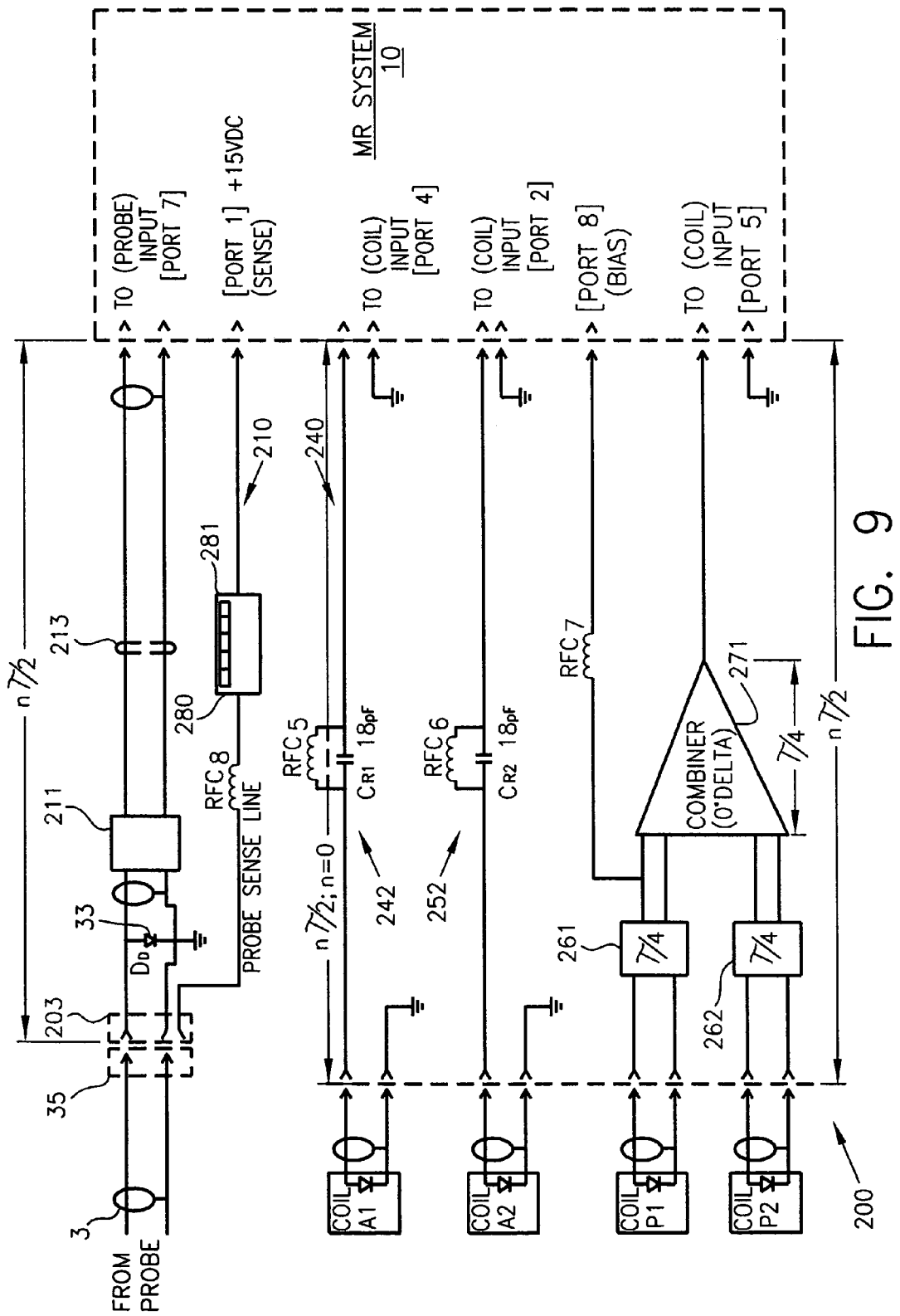
FIG. 9 is a schematic diagram of an interface device according to yet another aspect of the presently preferred embodiment of the invention wherein, in its multiple-receiver version, the interface device has (i) a probe interface circuit for interfacing the intracavity probe of FIGS. 1-7 with a (probe) input port of an MR system equipped with its own preamplifier and (ii) an array interface circuit for interfacing a phased array coil system, such as the Gore® torso array, with the (coil) input ports of the MR system.

Output cable 3 is designed to connect coil loop 2 to an interface device for the intracavity probe 1. Such an interface device, such as either of the ones disclosed below, at its other end in turn connects to a probe input port of the MR system 10, as shown in FIGS. 8 and 9. Encased within an insulating sheath, output cable 3 has a shield conductor 31 and a center conductor 32 insulatively disposed therein. The shield conductor 31 connects to the junction node 22, and the center conductor 32 connects to a node of one of the drive capacitors 21 and 23 opposite junction node 22, as shown in FIG. 1. In addition, for reasons detailed below, output cable 3 preferably has an electrical length of $n(\lambda/2)+S_L$, where n is an integer, $\lambda$ is the wavelength of the operating frequency of MR system 10, and $S_L$ is a supplemental length.

FIG. 2 shows the intracavity probe 1 of the present invention in fully assembled form, and FIGS. 3-7 illustrate various partial cross-sectional views thereof. Intracavity probe 1 includes a flexible shaft 40 and inner and outer balloons 50 and 60. The shaft 40 has a distal end whose tip 41 is preferably substantially more flexible than the remainder of the shaft, and indeed may be bonded thereto as indicated at reference numeral 15. The use of such a flexible tip 41 will reduce not only the discomfort felt by the patient but also the likelihood of perforating nearby tissue during use of the probe.

Inner balloon 50 connects to the distal end of shaft 40 and encloses tip 41 thereof, as best shown in FIG. 3. Inner balloon 50 is generally cylindrical in shape except for a substantially planar section on its anterior surface 51. It can be anchored to shaft 40 by a clamp 16 and by an interference fit with the distal end of shaft 40. Coil loop 2 itself is preferably encased within 5K volt insulation over which shrink wrap or similar tubing is used, thus providing a double layer of insulation. A non-stretchable material 55, which is preferably composed of an adhesive-backed cloth, can then be used to attach the coil loop 2 to the anterior surface 51 of inner balloon 50, thus securing the coil loop 2 between the inner and outer balloons 50 and 60.

Figure 5:
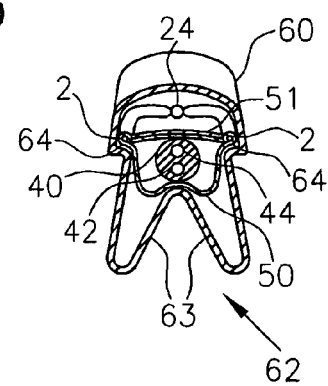
FIG. 5 is a cross-sectional view of the distal end of the intracavity probe taken through line 5-5 of FIG. 3 showing its outer and inner balloons, its coil loop situated between the balloons, and its shaft with the two lumens defined therein.
Figure 6:
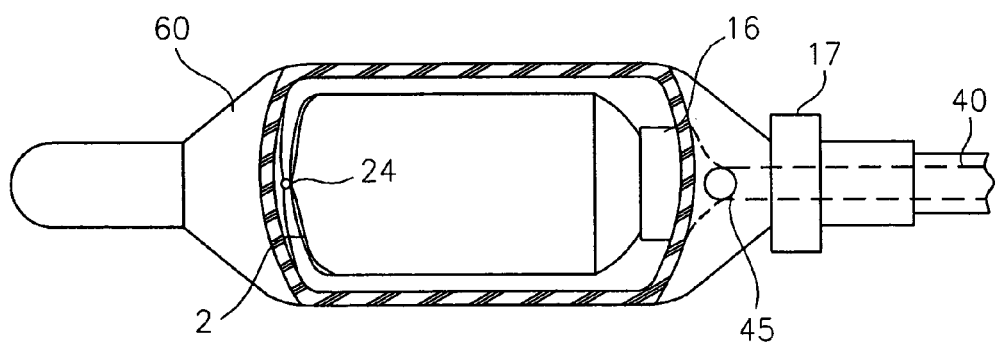
FIG. 6 is a cross-sectional view of the distal end of the intracavity probe taken through line 6-6 of FIG. 3 showing its coil loop situated atop an anterior surface of the inner balloon.

Outer balloon 60 also connects to the distal end of shaft 40, enclosing both coil loop 2 and inner balloon 50. It can be anchored to shaft 40 by a clamp 17 and by an interference fit with the distal end. Outer balloon 60 has anterior and posterior surfaces 61 and 62. The anterior surface 61 is preferably saddle-shaped to conformably fit against a correspondingly-shaped interior surface/contour of the cavity, which in the case of the prostate probe will be the rectal prostatic bulge inferior to the ampulla of the rectum. The posterior surface 62 features at least one pair of undulating folds 63 projecting therefrom. As described below, these folds 63 enable the outer balloon 60 to properly position the coil loop 2 in operative proximity to the rectal prostatic bulge of the patient when the inner balloon 50 is inflated, which optimizes the coupling between coil loop 2 and the target anatomy. In addition, as shown in FIG. 5, lateral indentations 64 are preferably provided within outer balloon 60 intermediate the anterior and posterior surfaces 61 and 62. These indentations 64 essentially form a shelf on which the sides of coil loop 2 rest during assembly of the probe 1. They essentially serve as a means of positioning the coil loop between those surfaces when balloons 50 and 60 are in the uninflated state. The balloons 50 and 60 are each preferably made of a medical-grade latex or other appropriate elastomeric material. Such material should, of course, be non-paramagnetic and exhibit low dielectric losses.

Figure 7:
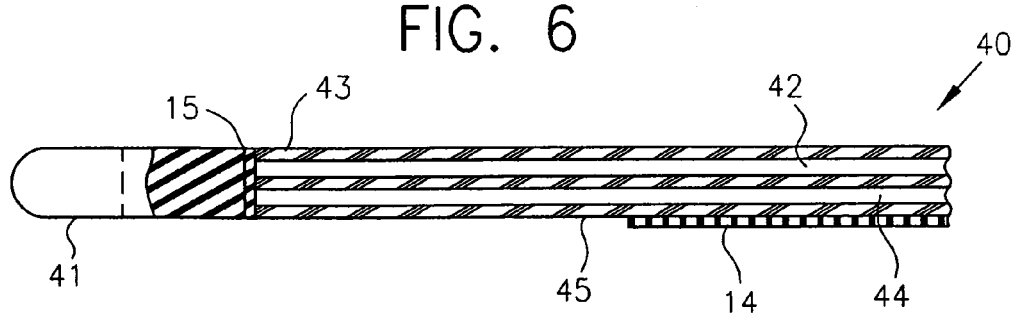
FIG. 7 is a cross-sectional view of the shaft of the intracavity probe of FIG. 2 illustrating the two lumens defined therein and a flexible tip at its distal end.

Flexible shaft 40 defines two lumens 42 and 44, as best shown in FIGS. 3, 4, 5 and 7. Within its cylindrical wall near its distal end, shaft 40 also defines a hole 43 in communication with lumen 42, as shown in FIG. 7. Lumen 42 and hole 43 together serve as a passageway for the air or other gas pumped into and expelled out of inner balloon 50 when inflated and deflated, respectively. Further away from its distal end, shaft 40 defines another hole 45 in its cylindrical wall. Lumen 44 and hole 45 act as the conduit through which output cable 3 is routed from coil loop 2. Output cable 3, as shown in FIG. 2, has a plug 35 at its proximal end to connect the intracavity probe 1 with the appropriate interface device.

Figure 4:
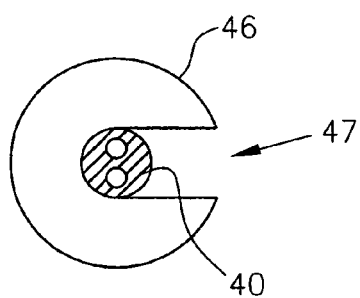
FIG. 4 is partial cross-sectional view of the intracavity probe taken through line 4-4 of FIG. 2 showing its shaft in cross-section and the two lumens defined therein and an anti-migration disc snapped onto the shaft.

Intracavity probe 1 further includes an anti-migration disc 46, an introducer 48, and a handle 49. Fixed to the proximal end of shaft 40, the handle 49 enables the probe 1 to be easily manipulated as its distal end, inclusive of outer balloon 60 secured thereon, is inserted into the rectum and appropriately aligned within the cavity as described below. The introducer 48, also referred to as a dilator element, is designed to be easily slid over the entire length of shaft 40. Preferably funnel-shaped, the introducer 48 can be used to manually dilate the anal sphincter to allow outer balloon 60 to be easily positioned within the cavity. Without introducer 48, the anal sphincter would contract around shaft 40 and interfere with the ability to rotationally and longitudinally position the intracavity probe 1 within the cavity. The anti-migration disc 46, composed of a semi-rigid plastic or other suitable polymer, is preferably semi-spherical in shape. As shown in FIGS. 2 and 4, the disc 46 defines a slot 47. This slot allows the disc 46 to be snapped onto shaft 40. When affixed to shaft 40 adjacent the anal sphincter after the probe has been inserted into the rectum, the anti-migration disc 46 prevents the probe 1 from migrating superiorly due to the normal peristaltic activity of the colon.

Intracavity probe 1 also includes a means for controlling inflation of inner balloon 50. The inflation control means preferably takes the form of a compressible inflator cuff 70, a tube 71, and a stop cock 72. A syringe of suitable size could be used in lieu of cuff 70. Tube 71 connects the inflator cuff 70, or syringe, to the lumen 42 at the proximal end of shaft 40. The stop cock 72 is connected in series with tube 71 and serves to control whether air is pumped to or released from inner balloon 50. The probe 1 also preferably features a scale 14 printed on an outer surface of shaft 40. Scale 14 provides an indication of not only the distance that shaft 40 has been inserted into the cavity but also the rotational orientation of the distal end for proper alignment of the saddle-shaped anterior surface 61 of outer balloon 60 with the prostate.

In operation, the distal end of intracavity probe 1 is inserted into the cavity via the rectum while inner balloon 50, and outer balloon 60 surrounding it, are in the uninflated state. Once the distal end is inserted, the introducer 48 can be used to keep the anal sphincter dilated and thereby enable shaft 40, and its balloon-enclosed distal end, to be easily manipulated within the cavity. With the distal end inserted and the introducer 48 in place, the scale 14 on shaft 40 can then serve as a guide to enable the clinician or other medical personnel to more accurately position the probe both rotationally and longitudinally within the cavity adjacent the region of interest. Once the intracavity probe 1 is correctly positioned, the introducer 48 can be pulled inferiorly along the shaft, thereby allowing the sphincter to contract around shaft 40. This contraction assists in holding the intracavity probe 1 in place. The anti-migration disc 46 can then be snapped onto the shaft 40 adjacent the sphincter to assure that the intracavity probe 1 stays in position during the MR scanning procedure.

Before inflating the balloons, the stop cock 72 must be switched to the open state. By pumping inflator cuff 70, the inner balloon 50 will inflate via tube 71, stop cock 72, and lumen 42 and hole 43 in shaft 40. As the inner balloon inflates, the non-stretchable material 55 that secures coil loop 2 to the anterior surface 51 of inner balloon 50 also focuses inflation of the inner balloon posteriorly so as to inflate into the undulating folds 63 of outer balloon 60. As the undulating folds 63 inflate, they soon force the posterior surface 62 (i.e., folds 63) of outer balloon 60 to abut against a wall of the cavity opposite the region of interest. As inner balloon 50 continues to inflate, the force of inflation is then directed towards the underside of the anterior surface 61 of outer balloon 60. The anterior surface 51 of inner balloon 50, with coil loop 2 attached thereto, thus forces the saddle-shaped anterior surface 61 of outer balloon 60 against the correspondingly-shaped interior contour of the cavity, namely, the prostatic region of the rectum. Once the balloons at the distal end are fully inflated, the coil loop 2 will be situated approximate the prostate gland for optimal reception of the MR signals therefrom during the MR scanning procedure. The stop cock 72 can then be switched to the closed position, thereby allowing the clinician to disconnect the inflator cuff 70 without deflating the balloons 50 and 60. The intracavity probe 1 can then be connected to the appropriate interface device via the plug 35 of output cable 3.

When the scanning procedure is completed, the clinician need only switch the stop cock 72 to the open position to deflate inner balloon 50 and outer balloon 60 therewith. Whether or not the anti-migration disc 46 is removed from shaft 40, the balloon-enclosed distal end can then be removed from the rectum merely by gently pulling on the handle 49 of the intracavity probe 1.

Alternatively, the intracavity probe 1 may employ a single balloon in lieu of the double balloon version described above. It may be composed of a single-ply medical-grade latex material or other suitable elastomeric material. In this arrangement, the balloon still connects to the distal end of flexible shaft 40, and the balloon will preferably have anterior and posterior surfaces identical to those described for the double balloon version. The coil loop 2, however, will ideally be bonded or otherwise secured to the underside of the anterior surface 61 of the balloon. The coil loop 2 could also be encapsulated within the anterior surface 61 during the process of manufacturing the balloon. For example, coil loop 2 could be placed on a surface of the balloon and then the balloon could be redipped to place another ply of material over the outer surface of the balloon, thus covering coil loop 2 and creating the anterior surface 61 described above. However manufactured, when the inflatable balloon is inserted into the cavity and inflated, the undulating folds 63 will press against the wall of the cavity opposite the region of interest. Upon full inflation of the balloon, its anterior surface 61 will then be forced against the correspondingly-shaped interior contour of the cavity thereby bringing the coil loop 2 into operative proximity with the region of interest (i.e., the prostate gland) wherefrom it can best receive the MR signals.

The invention further provides a preferred method of designing the intracavity probe 1. Variations on this method, which will become apparent to skilled artisans upon reading this document, are also contemplated by the present invention. The first step of the preferred method involves choosing the size of a loop of wire that will form the basis for coil loop 2. For an intracavity probe designed for imaging the prostate, the wire loop should be sized so that the distal end of the probe, inclusive of the two balloons between which coil loop 2 will be situated, can be inserted into the rectum with minimal discomfort to the patient. The next steps involve temporarily inserting a variable capacitor within the wire loop, and then subjecting the loop to the operating frequency of the MR system 10. For 3.0 Tesla scanners for which the present invention is particularly well suited, the operating frequency would be approximately 128 MHz. For the GEMS 3.0T Signa® scanner, the operating frequency is actually closer to 127.74 MHz. For the Siemens 3.0T scanner, the operating frequency is 123.2 MHz.

While the wire loop is being subjected to RF energy at the designated operating frequency, the variable capacitor should be adjusted to a value, hereinafter referred to as $C_{RV}$, at which the wire loop will resonate. Once resonance is achieved, the capacitive and inductive reactances of the wire loop will, of course, be equal in magnitude at the operating frequency. For the purposes of the following calculations, 10 picofarads (pF) is an ideal value for $C_{RV}$ to establish resonance within the wire loop according to the presently preferred method of designing the intracavity probe 1.

Once $C_{RV}$ has been established, the quality factor of the loop can be measured while the loop is operating under loaded conditions. There are several known techniques for measuring the quality factor. One such technique involves making an $S_{21}$ response measurement using two test probes and a network analyzer, with the two test probes being connected to ports 1 and 2, respectively, of the network analyzer. With the loops of the two test probes positioned at right angles to each other, the wire loop of the present invention is placed between them. This arrangement allows RF energy supplied to the loop of the first test probe to be induced within the wire loop, which in turn induces an RF signal in the loop of the second test probe. The two test probes then convey their respective RF signals to the network analyzer, which displays the resulting frequency response curve graphically in terms of amplitude versus frequency. Using the displayed signal, the quality factor can be ascertained by locating the center frequency of the frequency response curve and dividing it by the 3 dB bandwidth (i.e., the band between the 3 dB (half power) points at the high-pass and low-pass ends of the curve). For a 3.0 Tesla scanner, the quality factor of the loop will lie between 10 and 20. More typically, the quality factor of the loop under loaded conditions will be:

$$Q_{Loaded} = 15 \text{ (measured)}$$

The next step of the method involves determining the series resistance, $R_S$, of the loop. The series resistance represents the equivalent resistive losses exhibited by the loop due to its presence within the cavity of the patient. $R_S$ is thus not a physical component, only the effect the patient has on the loop. It reduces the quality of coil loop 2 by partially dissipating the energy within it. It can be calculated from the equation:

$$R_S = X_L/Q$$

where Q is the quality factor measured above and $X_L$ is the inductive reactance of the wire loop when loaded. As noted above, the capacitive and inductive reactances of the loop are equal in magnitude at resonance:

$$X_L = X_P$$

$$X_L = 2\pi f L_{COIL} \text{ and } X_P = 1/(2\pi f C_{RV})$$

where f is the operating frequency of the MR system 10. Consequently, the inductive reactance of the loop, $X_L$, can be calculated from:

$$X_L = 1/(2\pi f C_{RV}) = 1/(2\pi \times 128 \times 106 \times 10 \times 10^{-12}) = 124.34 \ \Omega.$$

Consequently, the series resistance of the loop will be:

$$R_S = X_L/Q_{Loaded} = 124.34 \ \Omega/15 = 8.29 \ \Omega.$$

The method also requires the step of matching the output impedance of intracavity probe 1 with the impedance required by the external circuit with which the intracavity probe shall interface. The external circuit can take the form of one of the interface devices disclosed herein, and will typically require an impedance of 50 Ω. Consequently, this step of the method includes devising an impedance matching network to match the impedance required by the external circuit, $R_P$, to the series resistance of the loop, $R_S$. In this impedance matching network, the quality of the series and parallel legs of the matching network, as represented by $Q_P = R_P/X_P$ and $Q_S = X_S/R_S$, are equal. Consequently, $R_S$ and $R_P$ are related by the equation:

$$R_P=(Q^2+1)R_S$$

where $R_P$ can also be referred to as the equivalent parallel resistance. Given that the quality of the series and parallel legs of the matching network are equal, the quality of the matching network can then be calculated from:

$$Q=Q_{S,P}=(R_P/R_S-1)^{1/2}=(50\ \Omega/8.29\ \Omega-1)^{1/2}=2.24.$$

The parallel reactance, $X_P$, associated with $R_P$ in the impedance matching network can then be calculated from:

$$X_P=R_P/Q=50\ \Omega/2.24=22.32\ \Omega.$$

The value of the matching capacitor can then determined from the parallel reactance:

$$C_P=1/(2\pi f X_P)=1/(2\pi\times128\times10^6\times22.32)=55.7\ pF.$$

Another step involves inserting two capacitors of the matching value into the wire loop in series with each other. These are the two drive capacitors, $C_{D1}$ and $C_{D2}$, respectively designated 21 and 23, shown in FIG. 1. Using the above calculations, the drive capacitors 21 and 23 together have an effective value of 27.85 pF. Junction node 22 is formed at the site at which drive capacitors 21 and 23 connect. The shield conductor 31 of output cable 3 connects to junction node 22, and the center conductor 32 connects to the node on the other side of either drive capacitor 21 or drive capacitor 23. Therefore, according to the above calculations, the value of drive capacitor 21, $C_{D1}$, is thus what enables the coil loop 2 to appear as a 50 ohm source to the interface device or other external circuit. This allows a 50 ohm coaxial cable to be used as the output cable 3.

A further step involves selecting a tuning capacitor, $C_{TUN}$, so that the total capacitance of the wire loop is equal to the resonance value, $C_{RV}$. The total capacitance of the wire loop, $C_{RV}$, can be determined from:

$$1/C_{RV}=1/C_{TUN}+1/C_{D1}+1/C_{D2}=1/C_{TUN}+2/C_D$$

where $C_D=C_{D1}=C_{D2}$. The value of the tuning capacitor, $C_{TUN}$, can then be calculated as follows:

$$C_{TUN} = (C_{RV} * C_D)/(C_D - 2C_{RV})$$
$$= (10\times10^{-12}F \times 55.7\times10^{-12}F)/(55.7\times10^{-12}F - 2\times10\times10^{-12}F)$$
$$= 15.6\ pF$$

The variable capacitor is then removed from the wire loop and replaced with the tuning capacitor, $C_{TUN}$. Designated as $C_T$ in FIG. 1, the tuning capacitor 24 is serially connected within the wire loop diametrically opposite the junction node 22. Junction node 22 thus forms a virtual ground for electrically balancing the coil loop, as the electric field there is effectively zero and the voltage drop across each drive capacitor is equal but opposite in sign. This configuration results in symmetry of the electric fields relative to the patient during the receive cycle of MR system 10. It renders coil loop 2 particularly sensitive to the magnetic field, but not the electric field, components of the MR signals emitted by the region of interest. It thus enables coil loop 2 to receive the MR signals with a greater signal-to-noise ratio than prior art probes. It also does so with greater safety, as the voltages induced in the coil loop will be equal and half of what they would otherwise be if the coil loop were totally unbalanced.

Due to the high operating frequency (e.g., 128 MHz for a 3.0T MR system) and very low operating Q (i.e., between 10-20) of coil loop 2, there is no need to tune coil loop 2 on a per patient or per-coil basis, unlike the probe disclosed in U.S. Pat. Nos. 5,476,095 and 5,355,087. On the basis of the above calculations including the quality factor of the loaded coil loop, the bandwidth of coil loop 2 will nominally be +/−4.25 MHz. Consequently, assuming the coil loop will be built with +/−2% components, the tuning shift from probe to probe should be a maximum of approximately +/−1.85 MHz, which is substantially less than the 3 dB bandwidth of the coil loop even without the effects of the low input impedance preamplifier explained below. The tuning is essentially fixed without material compromise due to the low Q of coil loop 2 under loaded conditions.

Output cable 3 preferably has an electrical length of $n(\lambda/2)+S_L$, where n is an integer, $\lambda$ is the wavelength of the operating frequency of MR system 10, and $S_L$ is a supplemental length. As best shown in FIG. 1, the entire length of output cable 3 extends from coil loop 2 to its plug 35. Plug 35 represents the point at which the output cable connects to the PIN diode 33, also referred to as the decoupling diode, of the interface device or other external circuit. The $n(\lambda/2)$ part yields a section whose length is one-half the operating wavelength, which will effectively appear as zero electrical length. The value of n will typically need only be equal to 1. as coil loop 2 will in practice always be reasonably close to the circuit to which it will connect. $S_L$ represents an additional section of output cable 3 whose inductive reactance is ideally equal in magnitude to the capacitive reactance of first capacitor 21 across which the terminals of cable 3 connect. The net effect is that the entire length of output cable 3 exhibits an inductive reactance equal to the capacitive reactance of first capacitor 21.

Supplement length $S_L$ thus inherently acts as an inductor, hereinafter referred to as $L_D$, which affects the operation of intracavity probe 1. During the transmit cycle of MR system 10, the MR system will decouple coil loop 2 of intracavity probe 1 from the MR system by forward biasing PIN diode 33 with a 200 mA current (see, e.g., FIG. 8). This will effectively short circuit PIN diode 33, and leave the inherent inductor, $L_D$, of output cable 3 and first drive capacitor 21, $C_{D1}$, as a parallel resonant circuit. The high impedance of this parallel resonant circuit approximates an open circuit, which effectively opens coil loop 2 and thus decouples the intracavity probe 1 from the probe input port of the host MR system 10. Conversely, during the receive cycle, the MR system will couple the intracavity probe 1 to the MR system by reverse biasing decoupling diode 33 with −5V DC. This will effectively cause output cable 3 to act as a 50 ohm transmission line rather than an inductor, $L_D$. This will allow coil loop 2 to detect the MR signals generated within the region of interest by the resonance-inducing RF pulse transmitted by the body coil of MR system 10 (or other external coil). The MR signals will then be passed to the interface device via the conductors of cable 3.

Drive capacitors $C_{D1}$ and $C_{D2}$ will typically have values in the range of approximately 62 pF to 82 pF. Similarly, tuning capacitor 24, $C_{TUN}$, will preferably be in the range of approximately 12 to 15 pF. Better decoupling (higher open-circuit impedance) during the transmit cycle can be obtained using a value for $C_{D1}$ in the lower end of the preferred range. Such a lower value for drive capacitor 21 would then also increase the source impedance that coil loop 2 presents to the interface device during the receive cycle. Furthermore, the exact length of $S_L$ will depend on the particular coil loop used within intracavity probe 1. For a coil loop that would be only lightly loaded during use, for example, drive capacitors of, say, 120 pF may be used, in which case $S_L$ would be shorter. Conversely, for a coil loop that would be more heavily loaded, drive capacitors of 40 pF might be used, in which case $S_L$ would be longer.

The intracavity probe 1 described above is particularly well suited for use as an endorectal coil probe with the 3.0T MR systems produced by GEMS, although it should be understood that the probe can be used for other applications as well.

FIGS. 8 and 9 depict two other aspects of the preferred embodiment of the invention, both of which designed to interface intracavity probe 1 with the GEMS MR system. In its first aspect, the interface device interfaces the intracavity probe with one receiver of the MR system, and is thus referred to as the single-receiver version. In its second aspect, the interface device interfaces both intracavity probe 1 and an external coil to the MR system using multiple receivers, and is referred to as the multiple-receiver version. As is well known, the typical GEMS Signa® system features four receivers and eight input ports. Receiver 0 can connect to Ports 1 or 5, receiver 1 to Ports 2 or 6, receiver 2 to Ports 3 or 7, and receiver 3 to Ports 4 or 8. In the standard configuration, the GEMS MR system has a preamplifier in each input port, except for Ports 1 and 8.

Figure 10:
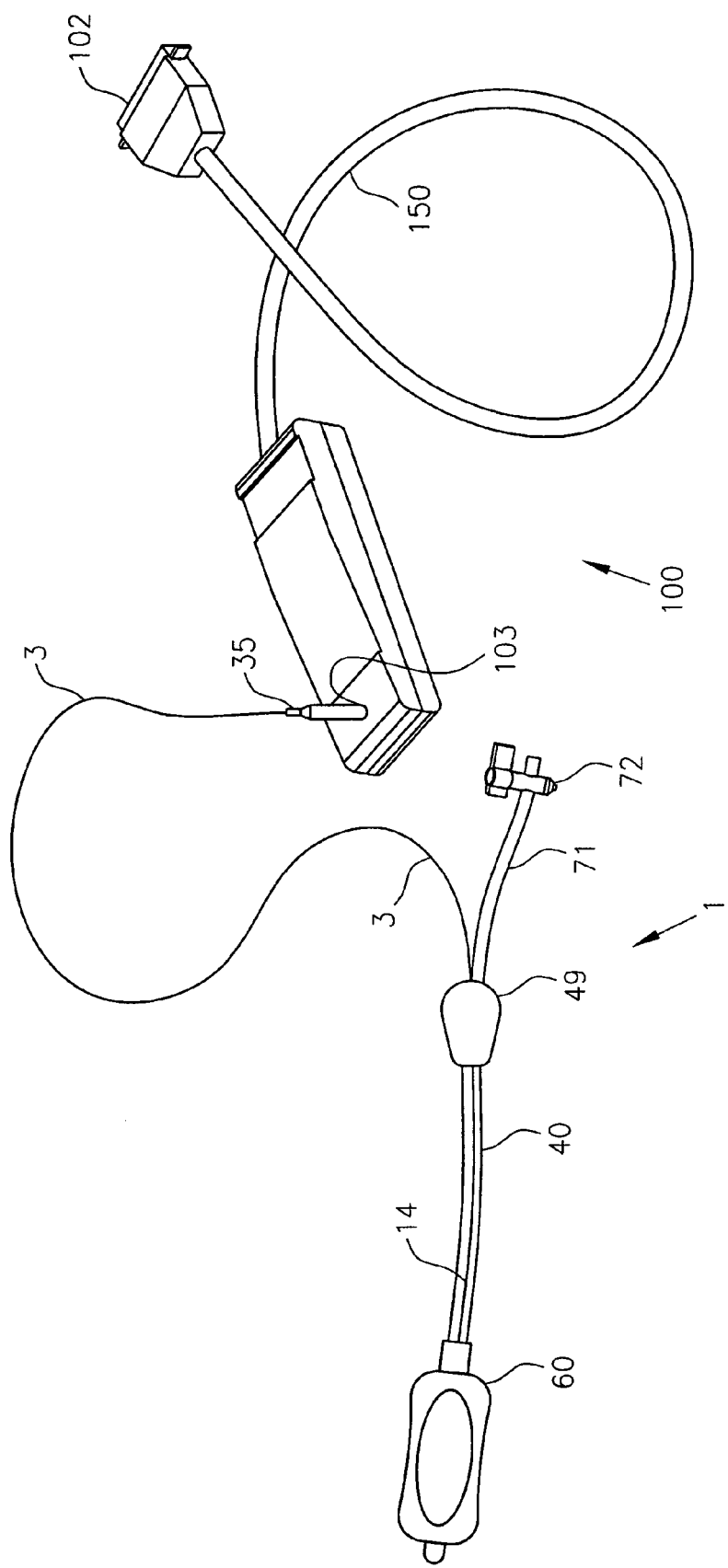
FIG. 10 is a perspective view of the interface device in its single-receiver version of FIG. 8, which is designed to interface the intracavity probe to the MR system via a (probe) input port thereof that is not equipped with a preamplifier.

FIGS. 8 and 10 illustrate the interface device, generally designated 100, according to its single-receiver version. By its connector 102, interface device 100 is designed to interconnect intracavity probe 1 via output cable 3 to Port 1 of the host MR system 10, which is not equipped with its own preamplifier. Consequently, interface device 100 includes PIN diode 33 and a preamplifier 101. PIN diode 33 is connected across the input socket 103 of interface device 100 into which plug 35 of output cable 3 plugs. This design choice allows PIN diode 33 to be physically remote from the intracavity probe 1, thus allowing it to be reused as part of the interface device after the probe 1 is disposed. The preamplifier includes a GASFET 110 and a series resonant input circuit 130. The series resonant circuit 130 includes an input capacitor $C_P$ and an input inductor $L_P$ at the junction of which the gate of GASFET 110 is also connected. The GASFET has its source connected to biasing resistor $R_B$ and its drain linked to coupling capacitor $C_C$ and an RF choke $RFC_2$. According well known circuit design principles, resistor $R_B$ should be selected so that the current flowing through GASFET 110 will provide a good gain and a low noise figure. $RFC_2$ allows DC power to be fed to the drain of GASFET 110 without shorting out the MR RF signals output by preamplifier 101 during the receive cycle of MR system 10. A cable trap 115 is preferably employed on the other side of capacitor $C_C$ to block undesirable cable currents.

When interface device 100 is connected to the MR system via probe cable 150 and connector 102, the drain is linked to Port 1 of MR system 10 via coupling capacitor $C_C$ and cable trap 115. The drain is also linked to a DC power source in MR system 10 via the RF choke $RFC_2$. Bypass capacitor $C_{B2}$ connects between this RF choke and ground, and therefore carries any non-DC components to ground. Interface device 100 also includes a bypass capacitor $C_{B1}$ and RF choke $RFC_1$. Bypass capacitor $C_{B1}$ connects between ground and a biasing line 121 with which MR system 10 is able to bias PIN diode 33. $C_{B1}$ thus serves to carry any non-DC components away from the biasing line and decoupling diode 33. $RFC_1$ connects between the anode of PIN diode 33 and bypass capacitor $C_{B1}$, and thus presents a high impedance to RF frequencies without appreciably limiting the flow of the biasing currents. Interface device 100 also preferably includes a preamp protection diode $D_{PP}$ and a bypass capacitor $C_{B3}$. Diode $D_{PP}$ protects preamplifier 101 during the transmit cycle of the MR system. Bypass capacitor $C_{B3}$ connects between the anode of the preamp protection diode $D_{PP}$ and ground. $RFC_3$ prevents any RF currents from preamplifier 101 from flowing to MR system 10, while allowing the flow of the biasing currents on biasing line 121.

During the transmit cycle, MR system 10 will forward bias diodes $D_D$ and $D_{PP}$ via biasing line 121. Situated across the connector 103 of device 100 into which plug 35 of output cable 3 plugs, PIN diode $D_D$ will thus decouple intracavity probe 1 as explained above. Meanwhile, preamp protection diode $D_{PP}$ will effectively short circuit the gate of GASFET 110, which prevents the transmitted RF pulse signal from damaging preamplifier 101. During the receive cycle, MR system 10 will reverse bias those diodes, effectively turning them off. The series resonant circuit 130 will provide optimum impedance to GASFET 110 when coil loop 2 is operating under loaded conditions. Coupled to the gate of GASFET 110, the series resonant circuit 130 will provide preamplifier 101 with a relatively low input impedance, which serves to broaden the frequency response of coil loop 2. This broader frequency response offsets the fixed tuning scheme, which makes the tuning of coil loop 2 far less critical when compared to the probe disclosed in U.S. Pat. Nos. 5,476,095 and 5,355,087. More specifically, with coil loop 2 acting as a 50 ohm input, series resonant circuit 130 will provide a high impedance (~1000 to 2000 ohms) to GASFET 110 while appearing as a very low impedance (~1 to 5 ohms) to coil loop 2. This will effectively cause coil loop 2 to decouple somewhat, which broadens its frequency response without sacrificing the signal-to-noise ratio. Along with its series resonant input circuit 130, preamplifier 101 will thus provide gain and impedance matching between the anode of decoupling diode 33 and Port 1 so that the MR signals detected by coil loop 2 are passed to Port 1 of the MR system with enhanced signal-to-noise ratio.

Interface device 100 also preferably features circuitry 160 to prevent the MR system 10 from performing a scanning procedure when the intracavity probe 1 is not connected to the interface device. Such circuitry 160 could create a driver fault within the MR system 10 to prevent it from undertaking a scan when the probe is disconnected. An audible alarm or display 161 as part of circuitry 160 through which to notify medical personnel of such a fault is also preferable.

Figure 11:
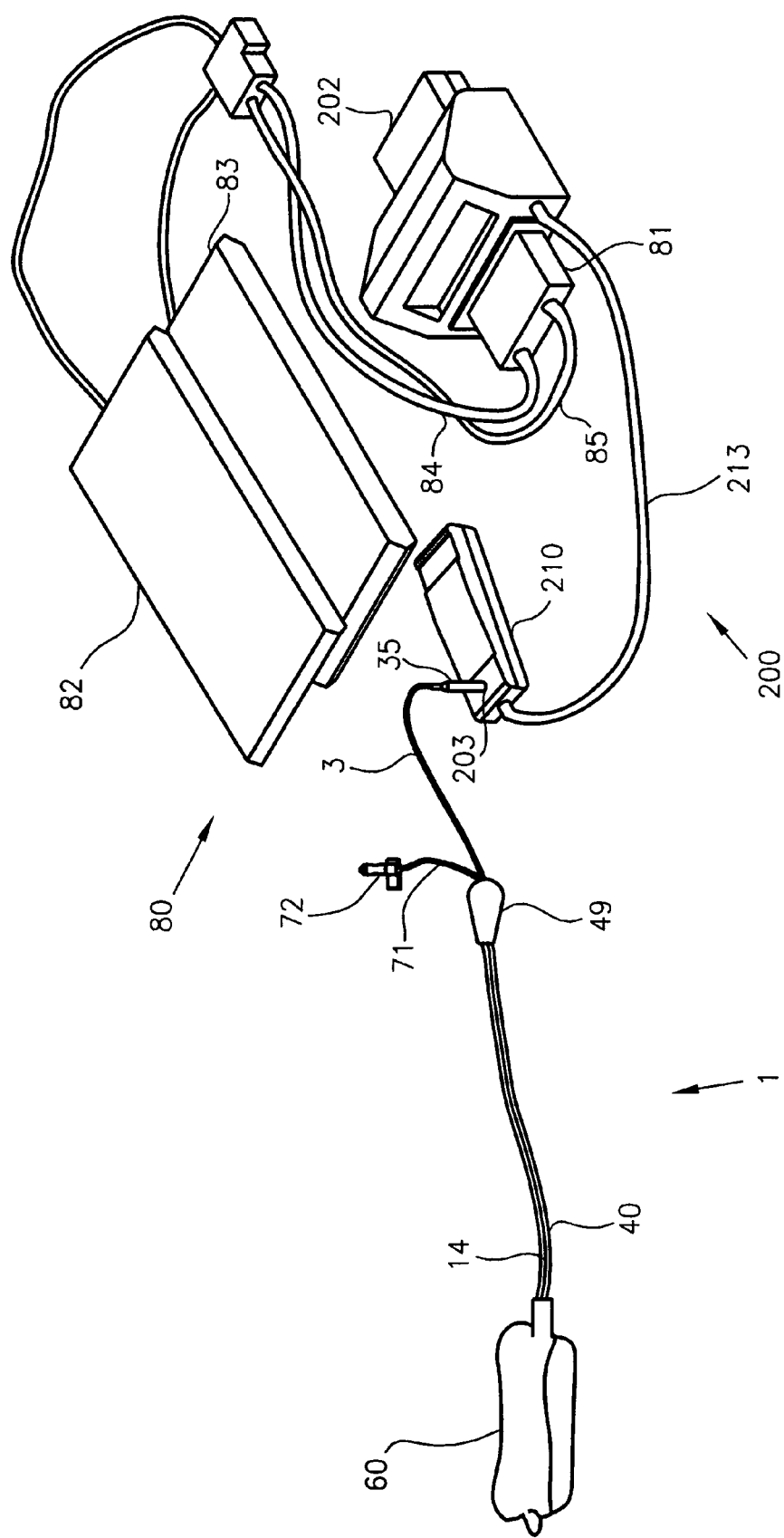
FIG. 11 is a perspective view of the interface device in its multiple-receiver version of FIG. 9, which is designed to interface the intracavity probe and a phased array coil system, such as the Gore® torso array, with the Phased Array Port of the MR system.

FIGS. 9 and 11 illustrate the interface device, generally designated 200, according to its multiple-receiver version. By its connector 202, interface device 200 is designed to interface not only intracavity probe 1 but also a phased array coil system 80 with the Phased Array Port of the GEMS 3.0T Signa® MR system. The Phased Array Port is typically composed of four ports (e.g., Ports 2, 4, 5, and 7), all of which are accessible via a single connector. The prior art Gore® torso array is one such phased array coil system 80 that itself can be plugged via its single connector 81 into the Phased Array Port. If the Gore® torso array were to be used as coil system 80, coil elements A1 and A2 of FIG. 9 would be the two surface coils in the anterior paddle 82, and coil elements P1 and P2 the two surface coils in the posterior paddle 83. Those two paddles each have two coil elements whose leads are routed by means of two cables 84,85 to single connector 81. It is by connector 81 that the Gore® torso array 80 normally plugs into the Phased Array Port of the host MR system, with each of its four coil elements being interconnected with one of the four system ports. Interface device 200, however, when used with intracavity probe 1 and the Gore® torso array, will interface five coil elements (i.e., coil loop 2 and coil elements A1, A2, P1 and P2) to the four-receiver Phased Array Port of MR system 10. Interface device 200 combines the four-coil torso array with the receive-only endorectal coil 1 to enable high resolution imaging of the prostate along with phased array imaging of the pelvic region.

Interface device 200 includes a probe interface circuit 210 and an array interface circuit 240. Probe interface circuit 210 includes PIN diode 33 and a cable trap 211. PIN diode 33 is connected across the input socket 203 of device 200 into which plug 35 of output cable 3 plugs. Probe cable 213, also referred to herein as circuit length 213, is used to link the decoupling diode 33—and therethrough coil loop 2 of intracavity probe 1—with a first port (i.e., Port 7) of MR system 10. Cable trap 211 prevents undesired current from flowing on the shield conductor of the probe cable. As shown in FIG. 9, the circuit length 213 preferably has an electrical length of $n(\lambda/2)$, where n is an integer and $\lambda$ is the wavelength of the operating frequency of the MR system. This makes circuit length 213 effectively appear to have zero electrical length.

The array interface circuit 240 is used to electrically interconnect phased array coil system 80 and MR system 10. It includes first and second series resonant networks 242 and 252, two ¼ wavelength networks 261 and 262, and a ¼ wavelength combiner 271. Assuming coil system 80 takes the form of the Gore® torso array, series resonant network 242 will convey the MR signals from anterior coil element A1 to a second port (i.e., Port 4) of MR system 10. Similarly, the other series resonant network 252 will pass the MR signals from anterior coil element A2 to a third port (i.e., Port 2). As illustrated in FIG. 9, one ¼ wavelength network 261 is situated to receive MR signals from posterior coil element P1, and the other ¼ wavelength network 262 is configured to receive MR signals from posterior coil element P2. Preferably of the Wilkinson type, the ¼ wavelength combiner 271 is connected to the outputs of both ¼ wavelength networks 261 and 262. It combines the MR signals received from those two networks and conveys the resulting MR signals to a fourth port (i.e., Port 5) of MR system 10.

The first series resonant network 242 includes capacitor $C_{R1}$ and RF choke $RFC_5$. Similarly, the second series resonant network 252 includes capacitor $C_{R2}$ and RF choke $RFC_6$. The values of $C_{R1}$ and $C_{R2}$ are selected so that each capacitor tunes out the inductance inherent in its respective circuit path. First and second networks 242 and 252 are thus series resonant at the operating frequency of MR system 10 (i.e., they act as if having a length of $n(\lambda/2)$ where n=0). This enables coil system 80 and MR system 10 to operate electrically as if there were no length to the networks 242 and 252. In addition, RF choke $RFC_5$ is disposed in parallel with capacitor $C_{R1}$, as choke $RFC_6$ is with capacitor $C_{R2}$. This is because, along the circuit paths of series resonant networks 242 and 252, MR system 10 will convey biasing signals to the decoupling diodes in coil system 80 for anterior coil elements A1 and A2. Chokes $RFC_5$ and $RFC_6$ allow those biasing signals to pass from Ports 4 and 2 to those decoupling diodes.

Furthermore, as shown in FIG. 9, the length of the circuit path from the input for coil element P1 (through network 261 and combiner 271) to Port 5 is ideally one-half the operating wavelength (i.e., $n\lambda/2$). The same length applies for the circuit path extending from the input for coil element P2 to Port 5. Consequently, these circuit paths will effectively appear as zero electrical length, which permits the beneficial effects of the low impedance preamplifier in Ports 5 to be reflected back to their respective inputs. In addition, MR system 10 conveys biasing signals to the decoupling diodes for posterior coil elements P1 and P2. An RF choke and related circuitry within combiner 271 and network 261 allow biasing signals to pass from Port 5 to the decoupling diode for coil element P2. An RF choke $RFC_7$ and related circuitry allow biasing signals to pass from Port 8 to the decoupling diode for coil element P1. The biasing signals for coil element P1 are sourced from Port 8 so that it is independent of that for coil element P2.

During the transmit cycle, MR system 10 will forward bias decoupling diode $D_D$ with the decoupling voltage, which is preferably superimposed on the signal line of cable 213. Situated across the connector 203 of device 200 into which plug 35 of output cable 3 plugs, PIN diode $D_D$ will thus decouple intracavity probe 1 as explained above. MR system 10 will also simultaneously forward bias the decoupling diodes of the four coil elements A1, A2, P1, and P2 in coil system 80. This will cause those decoupling diodes to short circuit, thereby yielding parallel resonant circuits of high impedance, which will effectively open circuit the four coil elements of coil system 80. In this manner, the host MR system 10 will thus decouple both the intracavity probe 1 and the torso array 80 from the Phased Array Port of the MR system. Conversely, during the receive cycle, MR system 10 will reverse bias PIN diode $D_D$ of probe 1 and the decoupling diodes of coil system 80, effectively turning them off. This will couple intracavity probe 1 and torso array 80 to the Phased Array Port. This will allow coil loop 2 and coil elements A1, A2, P1 and P2 to detect the MR signals emitted from their respective regions of interest (e.g., prostate and surrounding abdominal, thoracic and pelvic regions) in response to the resonance-inducing RF pulse(s). The MR signals will then be routed through interface device 200 in the aforementioned manner and passed via connector 202 to the Phased Array Port of the host MR system 10.

Interface device 200 also preferably features circuitry 280 to prevent the MR system from performing a scanning procedure when the intracavity probe 1 is not connected to the interface device. Such circuitry 280 could include a probe sense line connected to the socket 203 into which the plug 35 of intracavity probe 1 plugs. When the probe 1 is connected to interface device 200 (i.e., plug 35 inserted into socket 203), the probe sense line would be grounded. Circuitry 280 would then detect the ground and pass an appropriate signal to Port 1 to enable the MR system to begin the scanning procedure. Should the intracavity probe not be connected to the interface device, circuitry 280 would detect the resulting open circuit and respond by altering the state of Port 1 to prevent the MR system from undertaking the scan. An audible alarm or display 281 as part of circuitry 280 through which to notify the clinician of such a fault is also preferable. Various other methods of determining whether the probe is connected to the interface device are, of course, also contemplated by the present invention.

Figure 12:
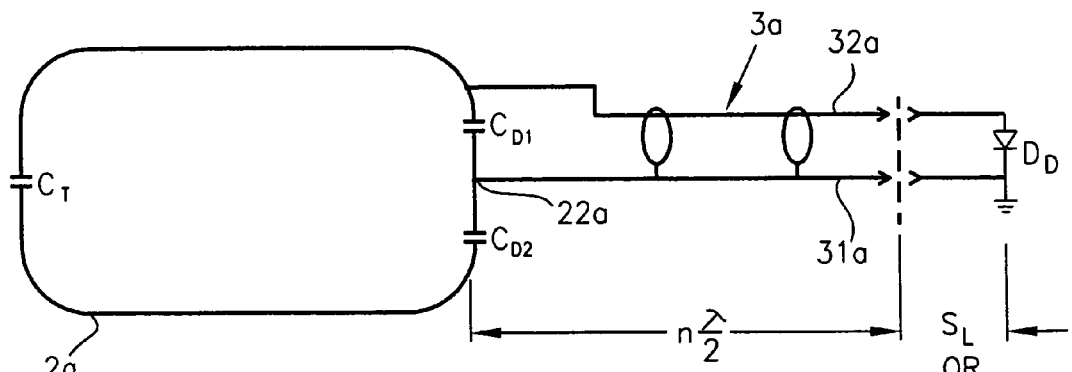
FIG. 12 is a schematic diagram of a coil loop and an output cable of an intracavity probe, and a decoupling diode of an interface device corresponding thereto, according to a first alternative embodiment of the invention.

FIG. 12 illustrates the intracavity probe, and the relevant part of the interface device corresponding thereto, according to a first alternative embodiment of the invention. Specifically, FIG. 12 shows coil loop 2a connected through output cable 3a to the decoupling diode $D_D$ of the interface device. Output cable 3a is unbalanced, with its shield conductor 31a connected to junction node 22a and its center conductor 32a connected to the node on the other side of drive capacitor $C_{D1}$. Unlike the previously disclosed preferred embodiment, however, output cable 3a has an electrical length of only $n(\lambda/2)$. This is because the supplemental length $S_L$ has been incorporated within the interface device. This can be accomplished as shown in FIG. 12, for example, by assuring that the electrical length from the input socket to the decoupling diode $D_D$ is equal to $S_L$. When output cable 3a of the probe is plugged into the interface device, the total electrical length from the coil loop 2a to PIN diode $D_D$ is then equal to $n(\lambda/2)+S_L$. Although this embodiment puts $S_L$ in the interface device rather than in its output cable 3a. it still allows the intracavity probe and its corresponding interface device to operate in the same manner as the presently preferred embodiment of the invention during both the transmit and receive cycles of the MR system.

Figure 13:
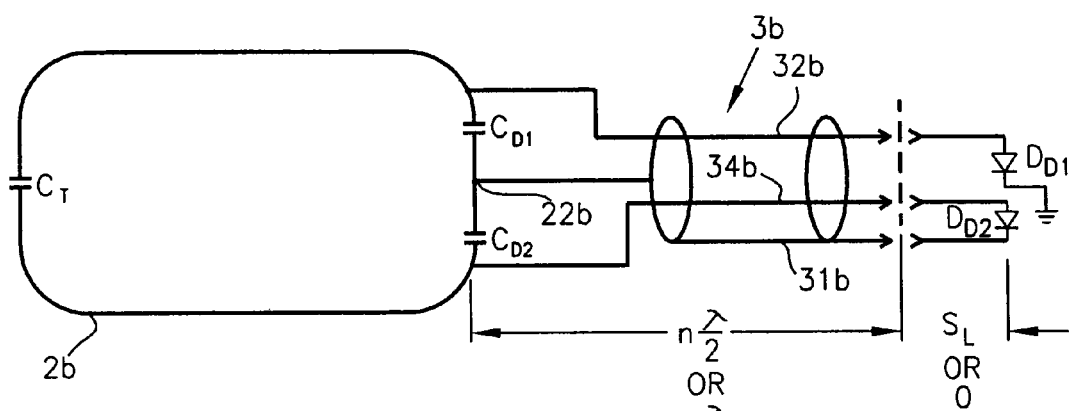
FIG. 13 is a schematic diagram of a coil loop and an output cable of an intracavity probe, and decoupling diodes of an interface device corresponding thereto, according to a second alternative embodiment of the invention.

FIG. 13 illustrates the intracavity probe, and the relevant part of the interface device corresponding thereto, according to a second alternative embodiment of the invention. Specifically, FIG. 13 shows coil loop $2b$ linked to the decoupling diodes $D_{D1}$ and $D_{D2}$ of the interface device through a balanced output cable $3b$. At one end of output cable $3b$. the first and second center conductors $32b$ and $34b$ are connected to the nodes on opposite sides of drive capacitors $C_{D1}$ and $C_{D2}$, respectively. When plugged into the input socket of the corresponding interface device, output cable $3b$ at its proximal end has its first and second center conductors $32b$ and $34b$ electrically linked to the anodes of diodes $D_{D1}$ and $D_{D2}$, respectively, with its shield conductor $31b$ grounded with the cathodes of the two decoupling diodes. Unlike the previously disclosed preferred embodiment, output cable $3b$ has an electrical length of only $n(\lambda/2)$, as $S_L$ has again been incorporated within the interface device. Such use of a balanced output cable $3b$ allows better decoupling (e.g., $2\times 1500\ \Omega$ across each drive capacitor) than the unbalanced output cable $3a$ used in the first alternative embodiment.

Figure 14:
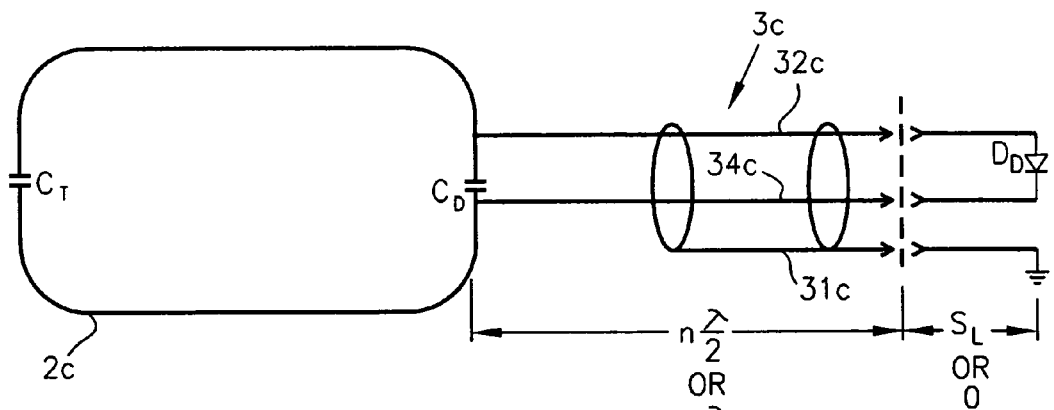
FIG. 14 is a schematic diagram of a coil loop and an output cable of an intracavity probe, and a decoupling diode of an interface device corresponding thereto, according to a third alternative embodiment of the invention.

FIG. 14 illustrates the intracavity probe, and the relevant part of the interface device corresponding thereto, according to a third alternative embodiment of the invention. The coil loop $2c$ of the probe is linked to the decoupling diode $D_D$ of the interface device through a balanced output cable $3c$. Unlike the previous embodiments, coil loop $2c$ is constructed with only one drive capacitor $C_D$, with the tuning capacitor $C_T$ positioned within the wire loop diametrically opposite it. The values of drive capacitor $C_D$ and tuning capacitor $C_T$ can be calculated generally according to the foregoing method so as to enable the coil loop $2c$ not only to appear as a 50 ohm source to the interface device but also to resonate at the operating frequency of the MR system. At one end of output cable $3c$. the first and second center conductors $32c$ and $34c$ are connected across drive capacitor $C_D$. When plugged into the input socket of the interface device, output cable $3c$ at its proximal end has its first and second conductors $32c$ and $34c$ electrically linked to the anode and cathode, respectively, of decoupling diode $D_D$ and its shield conductor $31c$ grounded with the interface device. Unlike the previously disclosed preferred embodiment, output cable $3c$ has an electrical length of only $n(\lambda/2)$, as $S_L$ has again been incorporated within the interface device.

As should be apparent to persons of ordinary skill in the field of magnetic resonance imaging and spectroscopy, the intracavity probe in any of the above embodiments may be constructed with two or more coil loops arranged in a phased array configuration. In addition, two or more coil loops in a single intracavity probe can be oriented cooperatively to provide quadrature coverage of the region of interest. The output cable of such intracavity probes will have to be modified accordingly to properly link the coil loops to the interface device.

The presently preferred and alternative embodiments for carrying out the invention have been set forth in detail according to the Patent Act. Persons of ordinary skill in the art to which this invention pertains may nevertheless recognize alternative ways of practicing the invention without departing from the spirit of the following claims. Consequently, all changes and variations which fall within the literal meaning, and range of equivalency, of the claims are to be embraced within their scope. Persons of such skill will also recognize that the scope of the invention is indicated by the following claims rather than by any particular example or embodiment discussed in the foregoing description.

Accordingly, to promote the progress of science and the useful arts, we secure for ourselves by Letters Patent exclusive rights to all subject matter embraced by the following claims for the time prescribed by the Patent Act.

What is claimed is:

1. An intracavity probe for use with a magnetic resonance (MR) system for obtaining images or spectra of a region of interest within a cavity of a patient, said intracavity probe comprising:
    (a) a coil loop for receiving MR signals from said region of interest, said coil loop having a plurality of capacitors therein, said plurality of capacitors including (i) a first drive capacitor and a second drive capacitor of approximately equal value serially connected within said coil loop and at a junction node thereof forming a virtual ground for electrically balancing and impedance matching said coil loop and (ii) a tuning capacitor serially connected within said coil loop diametrically opposite said junction node of said drive capacitors and having a value selected to resonate said coil loop at an operating frequency of said MR system; and
    (b) an output cable for connecting said coil loop to an interface device for said intracavity probe, said output cable at one end thereof being connected across one of said drive capacitors and at an other end thereof having a plug for connection to said interface device, said output cable having an electrical length of $n(\lambda/2)+S_L$ wherein n is an integer, $\lambda$ is a wavelength of said operating frequency of said MR system, and $S_L$ is a supplemental length whose reactance is of a same magnitude as a reactance of one of said drive capacitors.

2. The intracavity probe of claim 1 further comprising:
    (a) a flexible shaft having a tip at a distal end thereof, said tip being substantially more flexible than a remainder of said flexible shaft;
    (b) an inner balloon connected to said distal end of said flexible shaft and enclosing said tip thereof;
    (c) a non-stretchable material for securing said coil loop to an anterior surface of said inner balloon; and
    (d) an outer balloon connected to said distal end of said shaft enclosing both said inner balloon and said coil loop secured thereto, said outer balloon for use in positioning said inner balloon within said cavity of said patient;
    such that said non-stretchable material affects inflation of said inner balloon within said outer balloon to enable said coil loop therein to be positioned approximate said region of interest for optimal reception of said MR signals therefrom.

3. The intracavity probe of claim 2 wherein said non-stretchable material focuses inflation of said inner balloon to force a posterior surface of said outer balloon against a wall of said cavity then forcing an anterior surface of said outer balloon against a correspondingly-shaped interior contour of said cavity thereby bringing said coil loop approximate said region of interest for optimal reception of said MR signals therefrom.

4. The intracavity probe of claim 2 wherein said outer balloon has an anterior surface for conformably fitting to a correspondingly-shaped interior contour of said cavity.

5. The intracavity probe of claim 4 wherein said outer balloon has a posterior surface, opposite said anterior surface thereof, comprising at least a pair of undulating folds.

6. The intracavity probe of claim 5 further comprising a means for controlling inflation of said inner balloon, said inflation control means being connected to said flexible shaft through which a gas can be conveyed to inflate and deflate said inner balloon.

7. The intracavity probe of claim 6 wherein said inflation control means includes a stop cock for controlling passage of said gas therethrough and release of said gas therefrom.

8. The intracavity probe of claim 6 wherein said flexible shaft includes:
   (a) a first lumen for interconnecting said inflation control means and said inner balloon; and
   (b) a second lumen through which said output cable is routed from said coil loop to be made available for connection to said interface device for said intracavity probe.

9. The intracavity probe of claim 8 wherein said inflation control means comprises a compressible inflator cuff and a tube therewith connected to said first lumen of said flexible shaft to deliver said gas to said inner balloon upon compression of said inflator cuff.

10. The intracavity probe of claim 5 wherein said non-stretchable material focuses inflation of said inner balloon to force said undulating folds of said outer balloon posteriorly against a wall of said cavity then forcing said anterior surface of said outer balloon anteriorly against said correspondingly-shaped interior contour of said cavity thereby bringing said coil loop approximate said region of interest for optimal reception of said MR signals therefrom.

11. The intracavity probe of claim 10 wherein said anterior surface of said outer balloon is saddle-shaped and said correspondingly-shaped interior contour of said cavity is a rectal prostatic bulge of said patient.

12. The intracavity probe of claim 2 wherein said flexible shaft includes a scale printed on an outer surface thereof.

13. The intracavity probe of claim 2 wherein said inner and said outer balloons each comprise a non-paramagnetic, flame retardant, biocompatible medical grade material having low dielectric loss characteristics.

14. The intracavity probe of claim 2 further comprising an anti-migration disc attachable to said flexible shaft for preventing unwanted movement of said intracavity probe relative to said cavity of said patient.

15. The intracavity probe of claim 14 wherein said anti-migration means is a disc having a semi-spherical shape, said disc defining a slot for allowing said disc to be snapped onto said flexible shaft.

16. The intracavity probe of claim 2 further comprising a dilator element slidably mounted on said flexible shaft for dilating an orifice leading to said cavity to allow easy positioning of said intracavity probe within said cavity.

17. The intracavity probe of claim 2 wherein said outer balloon further comprises lateral indentations therein on which said coil loop at least partially rests when said outer balloon is uninflated.

18. The intracavity probe of claim 1 further comprising:
   (a) a flexible shaft;
   (b) an inflatable balloon connected to a distal end of said flexible shaft, said inflatable balloon having (i) an anterior surface conformable to a correspondingly-shaped interior contour of said cavity and (ii) a posterior surface comprising at least a pair of undulating folds; and
   (c) said coil loop secured within said inflatable balloon approximate an underside of said anterior surface thereof; such that when said inflatable balloon is inserted into said cavity and inflated said undulating folds thereof press against a wall of said cavity generally opposite said region of interest thus forcing said anterior surface of said inflatable balloon against said correspondingly-shaped interior contour of said cavity thereby bringing said coil loop approximate said region of interest for optimal reception of said MR signals therefrom.

19. The intracavity probe of claim 1 wherein said first and said second drive capacitors each have a value in a range of approximately 62 pF to 82 pF and said tuning capacitor has a value in a range of approximately 12 pF to 15 pF.

20. The intracavity probe of claim 1 wherein said interface device includes a PIN diode capable of being biased by said MR system so that said coil loop via said output cable can be (i) coupled to a signal processing port of said MR system during a receive cycle of said MR system and (ii) decoupled from said signal processing port during a transmit cycle of said MR system.

21. The intracavity probe of claim 20 wherein forward biasing of said PIN diode causes resonance of an inductance of said output cable and a capacitance of one of said drive capacitors to open circuit effectively said coil loop and thereby decouple said intracavity probe from said signal processing port of said MR system during said transmit cycle.

* * * * *

UNITED STATES PATENT AND TRADEMARK OFFICE
CERTIFICATE OF CORRECTION

PATENT NO. : 7,747,310 B2
APPLICATION NO. : 10/483945
DATED : June 29, 2010
INVENTOR(S) : George J. Misic and Edward J. Rhinehart Page 1 of 1

It is certified that error appears in the above-identified patent and that said Letters Patent is hereby corrected as shown below:

ON THE TITLE PAGES:
On page 1, in Item (56) under "U.S. PATENT DOCUMENTS", in Column 2 Line 3, delete "Fericot" and insert -- Ferciot --, therefor.
On page 2, in Item (56) under "FOREIGN PATENT DOCUMENTS", in Column 2 Line 13, delete "JP" and insert -- WO --, therefor.

Column 2, Line 29, delete "B1" and insert -- $B_1$ --, therefor.
Column 4, Line 54, delete "5,355,087." and insert -- 5,355,087, --, therefor.
Column 4, Line 62, delete "5,348,010." and insert -- 5,348,010, --, therefor.
Column 7, Line 29, delete "a" and insert -- an --, therefor.
Column 16, Line 24, delete "1." and insert -- 1, --, therefor.
Column 18, Line 58, delete "84,85" and insert -- 84, 85 --, therefor.
Column 20, Line 66, delete "3a." and insert -- 3a, --, therefor.
Column 21, Line 8, delete "cable 3b. the first" and insert -- cable 3b, the first --, therefor.
Column 21, Line 36, delete "3c." and insert -- 3c, --, therefor.

Signed and Sealed this
Twenty-sixth Day of April, 2011

David J. Kappos
*Director of the United States Patent and Trademark Office*